United States Patent
Brader (12)

(10) Patent No.: US 6,268,335 B1
(45) Date of Patent: Jul. 31, 2001

(54) INSOLUBLE INSULIN COMPOSITIONS

(75) Inventor: Mark Laurence Brader, Indianpolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/177,685

(22) Filed: Oct. 22, 1998

Related U.S. Application Data

(60) Provisional application No. 60/063,104, filed on Oct. 24, 1997, and provisional application No. 60/088,930, filed on Jun. 11, 1998.

(51) Int. Cl.[7] ............................. A61K 38/28; C07K 5/00; C07K 7/00
(52) U.S. Cl. .................................. 514/3; 514/4; 530/303; 530/304; 530/345; 424/491
(58) Field of Search ..................... 530/303, 304, 530/345; 514/314; 424/491

(56) References Cited

U.S. PATENT DOCUMENTS

| | | |
|---|---|---|
| 2,538,018 | 1/1951 | Krayenbühl et al. . |
| 2,801,953 | 8/1957 | Dorzbach et al. . |
| 2,849,370 | 8/1958 | Petersen et al. . |
| 3,060,093 | 10/1962 | Poulsen et al. . |
| 3,102,077 | 8/1963 | Christensen . |
| 3,684,791 | 8/1972 | Geiger et al. . |
| 3,865,325 | 2/1975 | Smyth . |
| 3,868,356 | 2/1975 | Smyth . |
| 3,868,358 | 2/1975 | Jackson . |
| 3,869,437 | 3/1975 | Lindsay . |
| 3,907,763 | 9/1975 | Brandenberg et al. . |
| 3,950,517 | 4/1976 | Lindsay ................................ 424/178 |
| 4,183,849 | 1/1980 | Hansen et al. . |
| 4,343,898 | 8/1982 | Markussen ............................ 435/71 |
| 4,400,465 | 8/1983 | Morihara ............................... 435/71 |
| 4,401,757 | 8/1983 | Morihara ............................... 435/71 |
| 4,489,159 | 12/1984 | Markussen ............................ 435/71 |
| 4,601,852 | 7/1986 | Obermeier et al. .................. 530/303 |
| 4,601,979 | 7/1986 | Andresen et al. ..................... 435/70 |
| 4,608,364 | 8/1986 | Grau ....................................... 514/4 |
| 4,959,351 | 9/1990 | Grau ....................................... 514/4 |
| 5,149,777 | 9/1992 | Hansen et al. ....................... 530/303 |
| 5,164,366 | 11/1992 | Balschmidt et al. .................... 514/3 |
| 5,430,016 | 7/1995 | Balschmidt et al. .................... 514/4 |
| 5,461,031 * | 10/1995 | DeFelipps ............................... 514/4 |
| 5,474,978 | 12/1995 | Bakaysa et al. ........................ 514/4 |
| 5,514,646 | 5/1996 | Chance et al. .......................... 514/3 |
| 5,547,930 | 8/1996 | Balschmidt ............................. 514/3 |
| 5,618,913 | 4/1997 | Brange et al. ....................... 530/303 |
| 5,650,486 * | 7/1997 | DeFelipps ........................... 530/305 |
| 5,747,642 * | 5/1998 | DeFelipps ........................... 530/304 |
| 5,834,422 | 10/1998 | Balschmidt ............................. 514/3 |

FOREIGN PATENT DOCUMENTS

| | | |
|---|---|---|
| 0214826 | 3/1987 | (EP) . |
| 0375437 | 6/1990 | (EP) . |
| 0383472 | 8/1990 | (EP) . |
| 0709395 | 5/1996 | (EP) . |
| 0861851 | 9/1998 | (EP) . |
| 1-254699 | 10/1989 | (JP) . |
| 90/07522 | 7/1990 | (WO) . |
| 95/00550 | 1/1995 | (WO) . |
| 95/07931 | 3/1995 | (WO) . |
| 96/29344 | 9/1996 | (WO) . |
| 97/47312 | 12/1997 | (WO) . |
| 98/34953 | 8/1998 | (WO) . |

OTHER PUBLICATIONS

Wittingham et al., *Biochemistry*, 36, 1997, pp. 2826–2831.*
Simkin, R.D., et al., "Precipitation and Crystallization of Insulin in the Presence of Lysozyme and Salmine," *Biochem. Biophys. Acta*, 200:385–394 (1970).
Galloway, John A., et al., "Mixtures of Intermediate–Acting Insulin (NPH and Lente) with Regular Insulin: An Update," Insulin Update: 1992, Proceedings of a Symposium, Key Biscayne, Florida, Dec. 5–7, 1981, Excerpta Medica, Princeton, N.J. (1982).
Chen, Ing–Jun, et al., "Application of Mugiline β to the Preparation of Isophane Insulin," *Proc. Natl. Sci. Counc. ROC (A)*, vol. 6, No. 3, 185–189 (1982).
Fullerton, W. Wardle, et al., "Insulin Crystallization in the Presence of Basic Proteins and Peptides," *Biochim. Biophys. Acta*, 214:141–147 (1970).
Scott and Fisher, *j. Pharmacol. Exp. Ther.*, 58:78 (1936).
Hagedorn, et al., *J. Am. Med. Assn.*, 106:177–180 (1936).
Krayenbühl and Rosenberg, *Rep. Steno. Mem. Hosp. Nor. Insulinlab.*, 1:60 (1946).
Harding, et al., "The Crystal Structure on Insulin: II. An Investigation of Rhombohedral Zinc Insulin Crystals and a Report of other Crystalline Forms," *J. Mol. Biol.*, 16:212–226 (1966).
Wallhauser, K–H, "Antimicrobial Preservatives in Europe," Int'l. Sympos. Preservatives in Biological Products, San Francisco, vol. 24:9–28 (S. Karger, Basel, 1974).

(List continued on next page.)

Primary Examiner—Avis M. Davenport
(74) Attorney, Agent, or Firm—Andrea C. Walsh; James J. Kelley

(57) ABSTRACT

The present invention relates to insoluble compositions containing acylated proteins selected from the group consisting of acylated insulin, acylated insulin analog, and acylated proinsulin, and formulations thereof. The formulations are suitable for parenteral delivery or other means of delivery, to a patient for extended control of blood glucose levels. More particularly, the present invention relates to compositions comprised of an acylated protein complexed with zinc, protamine, and a phenolic compound such that the resulting microcrystal is analogous to the neutral protamine Hagedorn (NPH) insulin crystal form. Surprisingly, it has been discovered that compositions of such acylated proteins have therapeutically superior subcutaneous release pharmacokinetics, and more extended and flatter glucodynamics, than presently available commercial preparations of NPH insulin. Yet, the present crystals retain certain advantageous properties of NPH crystals, being readily able to be resuspended and also mixable with soluble insulins.

24 Claims, 1 Drawing Sheet

OTHER PUBLICATIONS

Chance, R.E., et al., "The Production of Human Insulin using Recombinant DNA Technology and a New Chain Combination Procedure," Peptides: Sythesis, Structure, Function, Proceeding of 7$^{th}$ American Peptide Symposium, Rich, D.H. and Gross, E., Eds., Pierce Chemical Company (1981).

Derewenda, et al., *Nature*, 338:13,594–596 (Apr. 1989).

Dodson, et al., *Phil Trans. R. Soc. Lond. A*, 345, 153–164 (1993).

Myers, S.R., et al., "Acylation of Human Insulin with Palmitic Acid Extends the Time Action of Human Insulin in Diabetic Dogs", *Diabetes*, 46:637–642 (1997).

Whittingham, J.L., et al., *Biochemistry* 36:2826–2831 (1997).

Whittingham, J.L., et al., *Biochemistry* 37:11516–11523 (1998).

DeFelippis, M.R., et al., Preparation and Characterization of a Cocrystalline Suspension of [LysB28,ProB29]–Human Insulin Analog, *J. Phrarmaceut. Sci.*, 87:170–176 (1998).

Hashimoto, M., et al., "Synthesis of palmitoyl derivatives of insulin and their biological activities," *Pharmaceut. Res.* 6:171 (1989).

* cited by examiner

INSOLUBLE INSULIN COMPOSITIONS

This application claims priority to U.S. Provisional Application Ser. No. 60/063104, filed on Oct. 24, 1997, and U.S. Provisional Application Ser. No. 60/088,930, filed Jun. 11, 1998.

BACKGROUND OF THE INVENTION 1. Field of the Invention

This invention is in the field of human medicine. More particularly, this invention is in the field of pharmaceutical treatment of the diseases of diabetes and hyperglycemia. 2. Description of Related Art It has long been a goal of insulin therapy to mimic the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained delivery of insulin to regulate hepatic glucose output for maintaining optimal fasting blood glucose.

Accordingly, effective therapy for people with diabetes generally involves the combined use of two types of exogenous insulin formulations: a rapid acting meal time insulin provided by bolus injections and a long-acting, so-called, basal insulin, administered by injection once or twice daily to control blood glucose levels between meals. An ideal basal insulin will provide an extended and "flat" time action—that is, it will control blood glucose levels for at least 12 hours, and preferably for 24 hours or more, without significant risk of hypoglycemia. Furthermore, an ideal basal insulin should be mixable with a soluble meal-time insulin, and should not cause irritation or reaction at the site of administration. Finally, basal insulin preparations that are suspension formulations should be able to be readily, and uniformly resuspended by the patient prior to administration.

As is well understood by those skilled in this art, long-acting insulin formulations have been obtained by formulating normal insulin as microcrystalline suspensions for subcutaneous injection. Examples of commercial basal insulin preparations include NPH (Neutral Protamine Hagedorn) insulin, protamine zinc insulin (PZI), and ultralente (UL). NPH insulin is the most widely-used insulin preparation, constituting from 50 to 70 percent of the insulin used worldwide. It is a suspension of a microcrystalline complex of insulin, zinc, protamine, and one or more phenolic preservatives. NPH insulin preparations are commercially available incorporating human insulin, pork insulin, beef insulin, or mixtures thereof. Also, NPH-like preparations of a monomeric insulin analog, LysB298,ProB29-human insulin analog, are known in the art [abbreviated herein as "NPL": De Felippis, M. R., U.S. Pat. No. 5,461,031, issued Oct. 24, 1995; De Felippis, M. R., U.S. Pat. No. 5,650,486, issued Jul. 22, 1997; and De Felippis, M. R., U.S. Pat. No. 5,747,642, issued May 5, 1998].

NPH insulin microcrystals possess a distinctive rod-shaped morphology of typical dimensions about 5 microns long by 1 micron thick and 1 micron wide. The extended duration of action of NPH insulin microcrystals results from their slow absorption from the subcutaneous injection site.

Therapy using currently-available NPH insulin preparations fails to provide the ideal "flat" pharmacokinetics necessary to maintain optimal fasting blood glucose for an extended period of time between meals. Consequently, treatment with NPH insulin can result in undesirably high levels of insulin in the blood, which may cause life-threatening hypoglycemia.

In addition to failing to provide an ideal flat pharmacokinetic profile, the duration of action of NPH insulin also is not ideal. In particular, a major problem with NPH therapy is the "dawn phenomenon" which is hyperglycemia that results from the loss of effective glucose control overnight while the patient is sleeping. These deficiencies in glycemic control contribute to serious long-term medical complications of diabetes and impose considerable inconvenience and quality-of-life disadvantages to the patient.

Protamine zinc insulin (PZI) has a composition similar to NPH, but contains higher levels of protamine and zinc than NPH. PZI preparations may be made as intermediate-acting amorphous precipitates or long-acting crystalline material. PZI, however, is not an ideal basal insulin pharmaceutical because it is not mixable with a soluble meal-time insulin, and the high zinc and protamine can cause irritation or reaction at the site of administration.

Human insulin ultralente is a microcrystalline preparation of insulin having higher levels of zinc than NPH, and not having either protamine or a phenolic preservative incorporated into the microcrystal. Human ultralente preparations provide moderate time action that is not suitably flat, and they do not form stable mixtures with insulin. Furthermore, they are difficult to resuspend.

There have been attempts to address the perceived inadequacies of known insulin suspensions. Fatty acid-acylated insulins have been investigated for basal control of blood glucose [Havelund, S., et al., WIPO publication WO95/07931, Mar. 23, 1995]. Their extended time action is caused by binding of the fatty acyl portion of these molecules to serum albumin. The fatty acyl chain lengths of these molecules is such as to take advantage of the fatty acid binding capability of serum albumin. The fatty acid chains used in fatty acid-acylated insulins are typically longer than about ten carbon atoms, and chain lengths of fourteen and sixteen carbon atoms are optimal for binding to serum albumin and extending time action.

Unlike NPH insulin, which is insoluble, the aforementioned fatty acid-acylated insulins are soluble at the usual therapeutic concentrations of insulin. However, the time action of these preparations may not be sufficiently long enough, or flat enough, to provide ideal basal control, and they are less potent than insulin, thereby requiring administration of greater amounts of the drug agent [Radziuk, J., et al., *Diabetologia* 41:116–120, 489–490 (1998)].

Whittingham, J. L., et al. [*Biochemistry* 36:2826–2831 (1997)] crystallized B29-Nε-tetradecanoyl-des(B30)-human insulin analog as a hexamer complex with zinc and phenol for the purpose of structural studies by X-ray crystallography. The hexamer was found to be in the R6 conformation, and to have certain properties different from hexamers of human insulin. Whittingham, et al. do not disclose any pharmaceutical or pharmacological properties of the crystal that was formed, nor do they suggest that such a crystal would have any advantageous properties for treating diabetes or hyperglycemia. It is not possible to predict from Whittingham, et al. whether protamine-containing crystals of the NPH type could be formed with derivatized insulins and insulin analogs, or what the pharmacokinetics or pharmacodynamic response of such crystals would be.

Thus, there remains a need to identify insulin preparations that have flatter and longer time action than NPH insulin, that are mixable with soluble, meal-time insulins, that can be readily resuspended, and that do not pose risk of irritation or reaction at the site of administration.

SUMMARY OF THE INVENTION

I have unexpectedly observed that when insulin is made less soluble by derivatizing one or more of its reactive side groups, the derivatized insulin can be incorporated into NPH-like crystals with protamine. When the derivatized protein is precipitated or crystallized, the rate at which the insulin derivative dissolves from the solid form is greatly reduced compared with the rate at which similar solid forms comprised of un-derivatized protein dissolve. I have furthermore discovered that crystals of derivatized proteins provide flatter and longer time action than do crystals comprised of un-derivatized protein. Additionally, I have surprisingly discovered that the benefits of flatter and longer time action can be obtained even from amorphous precipitates comprising derivatized protein.

Accordingly, in its broadest aspect, the present invention provides insoluble compositions comprising a derivatized protein selected from the group consisting of insulin derivatives, insulin analog derivatives, and proinsulin derivatives, wherein the derivatives are less soluble than the underivatized insulin, insulin analog, or proinsulin. The insoluble compositions also are comprised of a complexing compound, a hexamer-stabilizing compound, and a divalent metal cation. These insoluble compositions are useful for treating diabetes and hyperglycemia, and provide the advantages of having flatter and longer time action than NPH insulin. Furthermore, they are mixable in a formulation with soluble protein and with soluble derivatized protein. The insoluble compositions of the present invention are in the form of amorphous precipitates, and also more preferably, in the form of microcrystals.

More specifically, the present invention provides microcrystalline forms of fatty acid-acylated proteins that are useful for treating diabetes and hyperglycemia. These microcrystals comprise a fatty acid-acylated protein selected from the group consisting of fatty acid-acylated insulin, fatty acid-acylated insulin analog, and fatty acid-acylated proinsulin, protamine, a phenolic preservative, and zinc. Such microcrystals will provide both flatter and longer time action than NPH insulin, and are mixable with soluble proteins and soluble derivatized proteins.

The invention provides aqueous suspension formulations comprising the insoluble composition and an aqueous solvent. Such suspension formulations may contain, optionally, a soluble protein, such as human insulin, or a soluble analog of human insulin, such as a monomeric insulin analog, that control blood glucose immediately following a meal. The microcrystalline formulations of fatty acid-acylated insulins have superior pharmacodynamics compared with human insulin NPH. The present invention is distinct from previous fatty acid-acylated insulin technology in that the extension of time action of the present invention does not rely necessarily on albumin-binding, though albumin binding may further protract the time action of certain of the compositions of the present invention.

The invention also pertains to a process for preparing the insoluble compositions, and a method of treating diabetes or hyperglycemia comprising administering a formulation containing an insoluble composition to a patient in need thereof in a quantity sufficient to regulate blood glucose levels in the patient.

Also part of the present invention are amorphous precipitates, comprising, in their broadest aspect, a derivatized protein selected from the group consisting of derivatized insulin, derivatized insulin analog, and derivatized proinsulin, protamine, a phenolic preservative, and zinc, wherein the derivatized protein is less soluble than the underivatized protein.

BRIEF DESCRIPTION OF THE DRAWING

The dissolution rate of pork insulin NPH (- - -) and of B29-Nε-octanoyl-human insulin microcrystals of this invention (—) are compared in FIG. 1.

DESCRIPTION OF THE INVENTION

Figure 1:
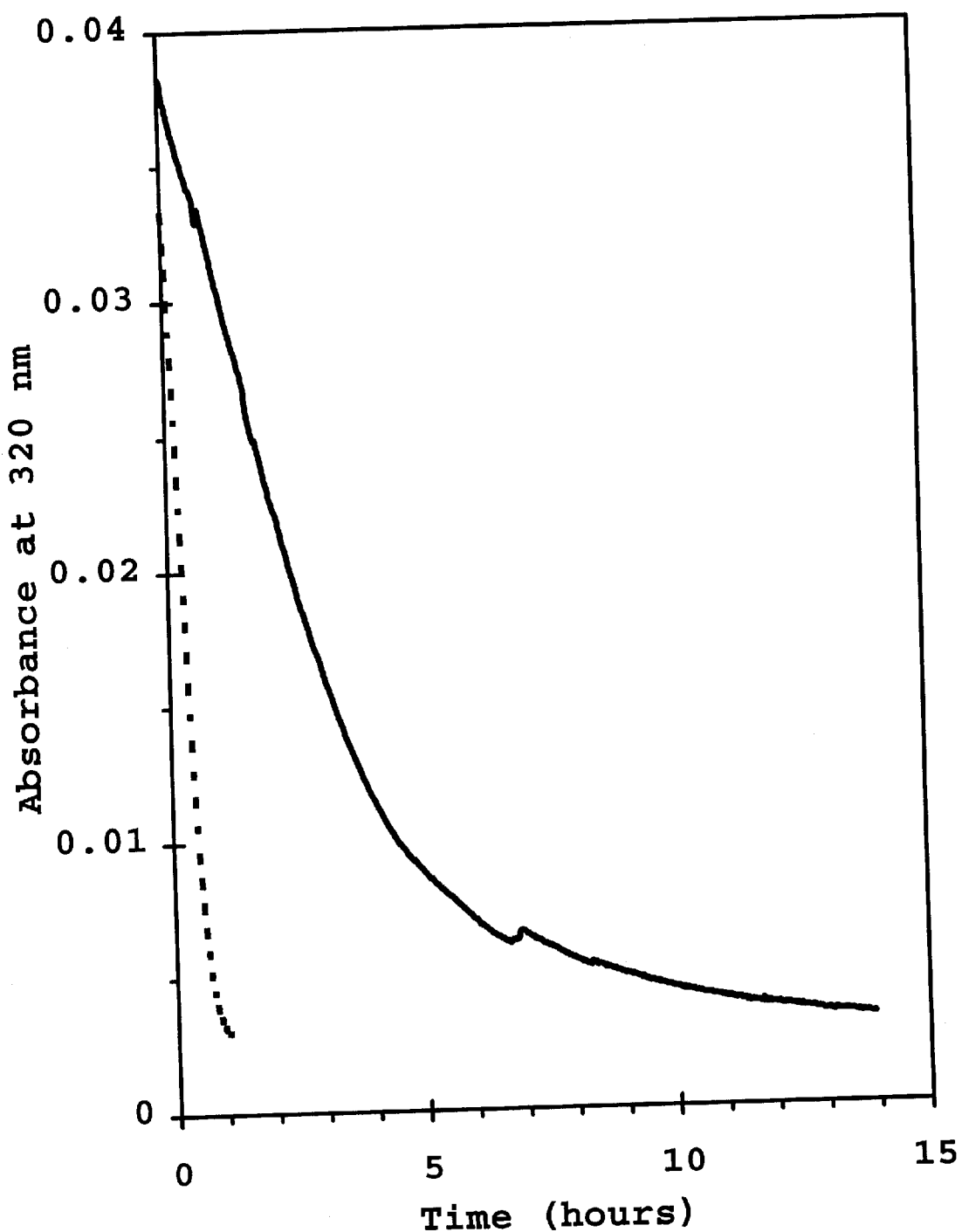

The term "insoluble composition" refers to matter in either a microcrystalline state or in an amorphous precipitate state. The presence of microcrystals or amorphous precipitate can be ascertained by visual and microscopic examination. Solubility depends on solvent, and a particular composition may be insoluble in one solvent, but soluble in another.

The term "microcrystal" means a solid that is comprised primarily of matter in a crystalline state, wherein the individual crystals are predominantly of a single crystallographic composition and are of a microscopic size, typically of longest dimension within the range 1 micron to 100 microns. The term "microcrystalline" refers to the state of being a microcrystal.

The term "amorphous precipitate" refers to insoluble material that is not crystalline in form. The person of ordinary skill can distinguish crystals from amorphous precipitate. The amorphous precipitates of the present invention have advantageous pharmacological properties in their own right, and also are intermediates in the formation of the microcrystals of the present invention.

The term "derivatized protein" refers to a protein selected from the group consisting of derivatized insulin, derivatized insulin analogs, and derivatized proinsulin that is derivatized by a functional group such that the derivatized protein is less soluble in an aqueous solvent than is the un-derivatized protein. Many examples of such derivatized proteins are known in the art, and the determination of solubility of proteins and derivatized proteins is well-known to the skilled person. Examples of derivatized insulin and insulin analogs include benzoyl, p-tolyl-sulfonamide carbonyl, and indolyl derivatives of insulin and insulin analogs [Havelund, S., et al., WO95/07931, published Mar. 23, 1995]; alkyloxycarbonyl derivatives of insulin [Geiger, R., et al., U.S. Pat. No. 3,684,791, issued Aug. 15, 1972; Brandenberg, D., et al., U.S. Pat. No. 3,907,763, issued Sep. 23, 1975]; aryloxycarbonyl derivatives of insulin [Brandenberg, D., et al., U.S. Pat. No. 3,907,763, issued Sep. 23, 1975]; alkylcarbamyl derivatives [Smyth, D. G., U.S. Pat. No. 3,864,325, issued Feb. 4, 1975; Lindsay, D. G., et al., U.S. Pat. No. 3,950,517, issued Apr. 13, 1976]; carbamyl, O-acetyl derivatives of insulin [Smyth, D. G., U.S. Pat. No. 3,864,325 issued Feb. 4, 1975]; cross-linked, alkyl dicarboxyl derivatives [Brandenberg, D., et al., U.S. Pat. No. 3,907,763, issued Sep. 23, 1975]; N-carbamyl, O-acetylated insulin derivatives [Smyth, D. G., U.S. Pat. No. 3,868,356, issued Feb. 25, 1975]; various O-alkyl esters [Markussen, J., U.S. Pat. No. 4,343,898, issued Aug. 10, 1982; Morihara, K., et al., U.S. Pat. No. 4,400,465, issued Aug. 23, 1983; Morihara, K., et al., U.S. Pat. No. 4,401,757, issued Aug. 30, 1983; Markussen, J., U.S. Pat. No. 4,489,159, issued Dec. 18, 1984; Obermeier, R., et al., U.S. Pat. No. 4,601,852, issued Jul. 22, 1986; and Andresen, F. H., et al., U.S. Pat. No. 4,601,979, issued Jul. 22, 1986]; alkylamide derivatives of insulin [Balschmidt, P., et al., U.S. Pat. No. 5,430,016, issued 4 July 1995]; various other derivatives of insulin [Lindsay, D. G., U.S. Pat. No. 3,869,437, issued Mar. 4, 1975]; and the fatty acid-acylated proteins that are described herein.

The term "acylated protein" as used herein refers to a derivatized protein selected from the group consisting of insulin, insulin analogs, and proinsulin that is acylated with an organic acid moiety that is bonded to the protein through an amide bond formed between the acid group of an organic acid compound and an amino group of the protein. In general, the amino group may be the α-amino group of an N-terminal amino acid of the protein, or may be the ε-amino group of a Lys residue of the protein. An acylated protein may be acylated at one or more of the three amino groups that are present in insulin and in most insulin analogs. Mono-acylated proteins are acylated at a single amino group. Di-acylated proteins are acylated at two amino groups. Tri-acylated proteins are acylated at three amino groups. The organic acid compound may be, for example, a fatty acid, an aromatic acid, or any other organic compound having a carboxylic acid group that will form an amide bond with an amino group of a protein, and that will cause the aqueous solubility of the derivatized protein to be lower than the solubility of the un-derivatized protein.

The term "fatty acid-acylated protein" refers to a an acylated protein selected from the group consisting of insulin, insulin analogs, and proinsulins that is acylated with a fatty acid that is bonded to the protein through an amide bond formed between the acid group of the fatty acid and an amino group of the protein. In general, the amino group may be the α-amino group of an N-terminal amino acid of the protein, or may be the ε-amino group of a Lys residue of the protein. A fatty acid-acylated protein may be acylated at one or more of the three amino groups that are present in insulin and in most insulin analogs. Mono-acylated proteins are acylated at a single amino group. Di-acylated proteins are acylated at two amino groups. Tri-acylated proteins are acylated at three amino groups. Fatty acid-acylated insulin is disclosed in a Japanese patent application 1-254,699. See also, Hashimoto, M., et al., *Pharmaceutical Research*, 6:171–176 (1989), and Lindsay, D. G., et al., *Biochemical J.* 121:737–745 (1971). Further disclosure of fatty acid-acylated insulins and fatty acylated insulin analogs, and of methods for their synthesis, is found in Baker, J. C., et al, U.S. Ser. No. 08/342,931, filed Nov. 17, 1994 and issued as U.S. Pat. No. 5,693,609, Dec. 2, 1997; Havelund, S., et al., WO95/07931, published Mar. 23, 1995, and a corresponding U.S. Pat. No. 5,750,497, May 12, 1998; and Jonassen, I., et al., WO96/29342, published Sep. 26, 1996. These disclosures are expressly incorporated herein by reference for describing fatty acid-acylated insulins and fatty acid-acylated insulin analogs and for enabling preparation of the same.

The term "fatty acid-acylated protein" includes pharmaceutically acceptable salts and complexes of fatty acid-acylated proteins. The term "fatty acid-acylated protein" also includes preparations of acylated proteins wherein the population of acylated protein molecules is homogeneous with respect to the site or sites of acylation. For example, Nε-mono-acylated protein, B1-Nα-mono-acylated protein, A1-Nα-mono-acylated protein, A1,B1-Nα-di-acylated protein, Nε, A1-Nα, di-acylated protein, Nε,B1-Nα, di-acylated protein, and Nε, A1,B1-Nα, tri-acylated protein are all encompassed within the term "fatty acid-acylated protein" for the purpose of the present invention. The term also refers to preparations wherein the population of acy-lated protein molecules has heterogeneous acylation. In the latter case, the term "fatty acid-acylated protein" includes mixtures of mono-acylated and di-acylated proteins, mixtures of mono-acylated and tri-acylated proteins, mixtures of di-acylated and tri-acylated proteins, and mixtures of mono-acylated, di-acylated, and tri-acylated proteins.

The term "insulin" as used herein, refers to human insulin, whose amino acid sequence and special structure are well-known. Human insulin is comprised of a twenty-one amino acid A-chain and a thirty-amino acid B-chain which are cross-linked by disulfide bonds. A properly cross-linked insulin contains three disulfide bridges: one between position 7 of the A-chain and position 7 of the B-chain, a second between position 20 of the A-chain and position 19 of the B-chain, and a third between positions 6 and 11 of the A-chain.

The term "insulin analog" means proteins that have an A-chain and a B-chain that have substantially the same amino acid sequences as the A-chain and B-chain of human insulin, respectively, but differ from the A-chain and B-chain of human insulin by having one or more amino acid deletions, one or more amino acid replacements, and/or one or more amino acid additions that do not destroy the insulin activity of the insulin analog.

"Animal insulins" are insulin analogs. Four such animal insulins are rabbit, pork, beef, and sheep insulin. The amino acid substitutions that distinguish these animal insulins from human insulin are presented below for the reader's convenience.

| | Amino Acid Position | | | |
|---|---|---|---|---|
| | A8 | A9 | A10 | B30 |
| human insulin | Thr | Ser | Ile | Thr |
| rabbit insulin | Thr | Ser | Ile | Ser |
| pork insulin | Thr | Ser | Ile | Ala |
| beef insulin | Ala | Ser | Val | Ala |
| sheep insulin | Ala | Gly | Val | Ala |

Another type of insulin analog, "monomeric insulin analog" is well-known in the art. Monomeric insulin analogs are structurally very similar to human insulin, and have activity similar or equal to human insulin, but have one or more amino acid deletions, replacements or additions that tend to disrupt the contacts involved in dimerization and hexamerization which results in their greater tendency to dissociate to less aggregated states. Monomeric insulin analogs are rapid-acting analogs of human insulin, and are disclosed, for example, in Chance, R. E., et al., U.S. Pat. No. 5,514,646, May 7, 1996; Brems, D. N., et al. *Protein Engineering*, 5:527–533 (1992); Brange, J. J. V., et al., EPO publication No. 214,826, published Mar. 18, 1987; Brange, J. J. V., et al., U.S. Pat. No. 5,618,913, Apr. 8, 1997; and Brange, J., et al., *Current Opinion in Structural Biology* 1:934–940 (1991). An example of monomeric insulin analogs is described as human insulin wherein Pro at position B28 is substituted with Asp, Lys, Leu, Val, or Ala, and wherein Lys at position B29 is Lys or is substituted with Pro, and also, AlaB26-human insulin, des(B28-B30)-human insulin, and des(B27)-human insulin. The monomeric insulin analogs employed as derivatives in the present crystals, or employed un-derivatized in the solution phase of suspension formulations, are properly cross-linked at the same positions as is human insulin.

Another group of insulin analogs for use in the present invention are those wherein the isoelectric point of the insulin analog is between about 7.0 and about 8.0. These analogs are referred to as "pi-shifted insulin analogs." Examples of such insulin analogs include ArgB31,ArgB32-human insulin, GlyA21,ArgB31,ArgB32-human insulin, ArgA0,ArgB31,ArgB32-human insulin, and ArgA0, GlyA21,ArgB31,ArgB32-human insulin.

Another group of insulin analogs consists of insulin analogs that have one or more amino acid deletions that do not significantly disrupt the activity of the molecule. This group of insulin analogs is designated herein as "deletion analogs." For example, insulin analogs with deletion of one or more amino acids at positions B1–B3 are active. Likewise, insulin analogs with deletion of one or more amino acids at positions B28–B30 are active. Examples of "deletion analogs" include des(B30)-human insulin, desPhe (B1)-human insulin, des(B27)-human insulin, des (B28–B30)-human insulin, and des(B1–B3)-human insulin. The deletion analogs employed as derivatives in the present crystals, or employed un-derivatized in the solution phase of suspension formulations, are properly cross-linked at the same positions as is human insulin.

Optionally, an insulin analog may have replacements of one or more of its amidated amino acids with other amino acids for the sake of chemical stability. For example, Asn and Gln may be replaced with Gly, Ser, Thr, Asp or Glu. In particular, AsnA18, AsnA21, or AsnB3, or any combination of those residues may be replaced by Gly, Asp, or Glu, for example. Also, GlnA15 or GlnB4, or both, may be replaced by either Asp or Glu. Preferred replacements are Asp at B21, and Asp at B3.

The term "proinsulin" means a single-chain peptide molecule that is a precursor of insulin. Proinsulin may be converted to insulin or to an insulin analog by chemical or, preferably, enzyme-catalyzed reactions. In proinsulin, proper disulfide bonds are formed as described herein. Proinsulin comprises insulin or an insulin analog and a connecting bond or a connecting peptide. A connecting peptide has between 1 and about 35 amino acids. The connecting bond or connecting peptide connects to a terminal amino acid of the A-chain and to a terminal amino acid of the B-chain by an α-amide bond or by two α-amide bonds, respectively. Preferably, none of the amino acids in the connecting peptide is cysteine. Preferably, the C-terminal amino acid of the connecting peptide is Lys or Arg. Proinsulin may have the formula X-B-C-A-Y or may have the formula X-A-C-B-Y, wherein X is hydrogen or is a peptide of from 1 to about 100 amino acids that has either Lys or Arg at its C-terminal amino acid, Y is hydroxy, or is a peptide of from 1 to about 100 amino acids that has either Lys or Arg at its N-terminal amino acid, A is the A-chain of insulin or the A-chain of an insulin analog, C is a peptide of from 1 to about 35 amino acids, none of which is cysteine, wherein the C-terminal amino acid is Lys or Arg, and B is the B-chain of insulin or the B-chain of an insulin analog.

A "pharmaceutically acceptable salt" means a salt formed between any one or more of the charged groups in a protein and any one or more pharmaceutically acceptable, non-toxic cations or anions. Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium.

The verb "acylate" means to form the amide bond between a fatty acid and an amino group of a protein. A protein is "acylated" when one or more of its amino groups is combined in an amide bond with the acid group of a fatty acid.

The term "fatty acid" means a saturated or unsaturated, straight chain or branched chain fatty acid, having from one to eighteen carbon atoms.

The term "C1 to C18 fatty acid" refers to a saturated, straight chain or branched chain fatty acid having from one to eighteen carbon atoms.

The term "divalent metal cation" refers to the ion or ions that participate to form a complex with a multiplicity of protein molecules. The transition metals, the alkaline metals, and the alkaline earth metals are examples of metals that are known to form complexes with insulin. The transitional metals are preferred. Zinc is particularly preferred. Other transition metals that may be pharmaceutically acceptable for complexing with insulin proteins include copper, cobalt, and iron.

The term "complex" has two meanings in the present invention. In the first, the term refers to a complex formed between one or more atoms in the proteins that form the complex and one or more divalent metal cations. The atoms in the proteins serve as electron-donating ligands. The proteins typically form a hexamer complex with divalent transition metal cations. The second meaning of "complex" in the present invention is the association between the complexing compound and hexamers. The "complexing compound" is an organic molecule that typically has a multiplicity of positive charges that binds to, or complexes with hexamers in the insoluble composition, thereby stabilizing them against dissolution. Examples of complexing compounds suitable in the present invention include protamine, surfen, various globin proteins [Brange, J., Galenics of Insulin, Springer-Verlag, Berlin Heidelberg (1987)], and various polycationic polymer compounds known to complex with insulin.

The term "protamine" refers to a mixture of strongly basic proteins obtained from fish sperm. The average molecular weight of the proteins in protamine is about 4,200 [Hoffmann, J. A., et al., Protein Expression and Purification, 1:127–133 (1990)]. "Protamine" can refer to a relatively salt-free preparation of the proteins, often called "protamine base." Protamine also refers to preparations comprised of salts of the proteins. Commercial preparations vary widely in their salt content.

Protamines are well-known to those skilled in the insulin art and are currently incorporated into NPH insulin products. A pure fraction of protamine is operable in the present invention, as well as mixtures of proteins. Commercial preparations of protamine, however, are typically not homogeneous with respect to the proteins present. These are nevertheless operative in the present invention. Protamine comprised of protamine base is operative in the present invention, as are protamine preparations comprised of salts of protamine, and those that are mixtures of protamine base and protamine salts. Protamine sulfate is a frequently used protamine salt.

The term "suspension" refers to a mixture of a liquid phase and a solid phase that consists of insoluble or sparingly soluble particles that are larger than colloidal size. Mixtures of NPH microcrystals and an aqueous solvent form suspensions. Mixtures of amorphous precipitate and an aqueous solvent also forms a suspension. The term "suspension formulation" means a pharmaceutical composition wherein an active agent is present in a solid phase, for example, a microcrystalline solid, an amorphous precipitate, or both, which is finely dispersed in an aqueous solvent. The finely dispersed solid is such that it may be suspended in a fairly uniform manner throughout the aqueous solvent by the action of gently agitating the mixture, thus providing a reasonably uniform suspension from which a dosage volume may be extracted. Examples of commercially available insulin suspension formulations include, for example, NPH, PZI, and ultralente. A small proportion of the solid matter in a microcrystalline suspension formulation may be amorphous. Preferably, the proportion of amorphous material is less than 10%, and most preferably, less than 1% of the solid matter in a microcrystalline suspension. Likewise, a small proportion of the solid matter in an amorphous precipitate suspension may be microcrystalline.

"NPH insulin" refers to the "Neutral Protamine Hagedorn" preparation of insulin. The meaning of such a term, and the methods for preparing such a preparation of insulin will be familiar to the person of ordinary skill in the insulin formulation art.

The term "aqueous solvent" refers to a liquid solvent that contains water. An aqueous solvent system may be comprised solely of water, may be comprised of water plus one or more miscible solvents, and may contain solutes. The more commonly-used miscible solvents are the short-chain organic alcohols, such as, methanol, ethanol, propanol, short-chain ketones, such as acetone, and polyalcohols, such as glycerol.

An "isotonicity agent" is a compound that is physiologically tolerated and imparts a suitable tonicity to a formulation to prevent the net flow of water across cell membranes that are in contact with an administered formulation. Glycerol, which is also known as glycerin, is commonly used as an isotonicity agent. Other isotonicity agents include salts, e.g., sodium chloride, and monosaccharides, e.g., dextrose and lactose.

The insoluble compositions of the present invention contain a hexamer-stabilizing compound. The term "hexamer-stabilizing compound" refers to a non-proteinaceous, small molecular weight compound that stabilizes the derivatized protein in a hexameric aggregation state. Phenolic compounds, particularly phenolic preservatives, are the best known stabilizing compounds for insulin and insulin derivatives. Such a hexamer-stabilizing compound stabilizes the insulin hexamer by binding to it through specific intermolecular contacts. Examples of such hexamer-stabilizing agents include: various phenolic compounds, phenolic preservatives, resorcinol, 4'-hydroxyacetanilide(tylenol), 4-hydroxybenzamide, and 2,7-dihyroxynaphthalene. Multi-use formulations of the insoluble compositions of the present invention will contain a preservative, in addition to a hexamer-stabilizing compound. The preservative used in formulations of the present invention may be a phenolic preservative.

The term "preservative" refers to a compound added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are benzalkonium chloride, benzethonium, chlorohexidine, phenol, m-cresol, benzyl alcohol, methylparaben, chlorobutanol, o-cresol, p-cresol, chlorocresol, phenylmercuric nitrate, thimerosal, benzoic acid, and various mixtures thereof. See, e.g., Wallhäusser, K.-H., *Develop. Biol. Standard*, 24:9–28 (1974) (S. Krager, Basel).

The term "phenolic preservative" includes the compounds phenol, m-cresol, o-cresol, p-cresol, chlorocresol, methylparaben, and mixtures thereof. Certain phenolic preservatives, such as phenol and m-cresol, are known to bind to insulin-like molecules and thereby to induce conformational changes that increase either physical or chemical stability, or both [Birnbaum, D. T., et al., *Pharmaceutical. Res.* 14:25–36 (1997); Rahuel-Clermont, S., et al., *Biochemistry* 36:5837–5845 (1997)].

The term "buffer" or "pharmaceutically acceptable buffer" refers to a compound that is known to be safe for use in insulin formulations and that has the effect of controlling the pH of the formulation at the pH desired for the formulation. The pH of the formulations of the present invention is from about 6.0 to about 8.0. Preferably the formulations of the present invention have a pH between about 6.8 and about 7.8. Pharmaceutically acceptable buffers for controlling pH at a moderately acidic pH to a moderately basic pH include such compounds as phosphate, acetate, citrate, arginine, TRIS, and histidine. "TRIS" refers to 2-amino-2-hydroxymethyl-1,3,-propanediol, and to any pharmacologically acceptable salt thereof. The free base and the hydrochloride form are two common forms of TRIS. TRIS is also known in the art as trimethylol aminomethane, tromethamine, and tris(hydroxymethyl)aminomethane. Other buffers that are pharmaceutically acceptable, and that are suitable for controlling pH at the desired level are known to the chemist of ordinary skill.

The term "administer" means to introduce a formulation of the present invention into the body of a patient in need thereof to treat a disease or condition.

The term "treating" refers to the management and care of a patient having diabetes or hyperglycemia, or other condition for which insulin administration is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder.

As mentioned above, the present invention provides insoluble compositions that have properties similar to NPH insulin in certain respects, and superior to NPH insulin in other respects. They are similar to NPH insulin in respect to their physical properties. A light microscope equipped with an oil immersion objective and a crossed polarizer was utilized to examine microcrystals comprised of B29-Nϵ-octanoyl-human insulin, zinc, protamine, and phenol, prepared according to the method of Preparation 18. Examination at 1000× magnification showed that the B29-Nϵ-octanoyl-human insulin microcrystals were single and rod-like, exhibiting a uniform crystal morphology. The sizes of these microcrystals fell generally within the range of approximately 2 microns long to 8 microns long. A direct comparison using this microscope showed that the morphology of these microcrystals appeared to be similar to that of commercially manufactured pork NPH microcrystals, which has elsewhere been described as rod-like. The size range of these B29-Nϵ-octanoyl-human insulin microcrystals was also similar to that of commercially manufactured NPH microcrystals, which generally have an average length of about 5 microns. The commercial manufacturing specification for the mean length of NPH microcrystals is from 1 micron to 40 microns.

The microcrystals of the present invention are, however, unexpectedly and unpredictably different from NPH insulin crystals in their dissolution properties, and in their time action. In particular, the microcrystals of the present invention dissolve much more slowly under conditions that simulate physiologic conditions than do NPH insulin crystals, and provide a longer and flatter profile of blood glucose control than does NPH insulin. This was demonstrated by the following experiments.

Certain derivatized proteins, in soluble form, were found to have time actions not significantly different from regular human insulin. Three groups of animals were used. Each animal in the first group received a dose (0.75 nmol/kg) of Humulin® R (soluble human insulin), each animal in the second group received a dose (0.75 nmol/kg) of soluble B29-Nε-octanoyl-human insulin ("C8-hI"), and each animal in the third group received a dose (0.75 nmol/kg) of soluble B29-Nε-decanoyl-human insulin ("C10-hI"). The experiments were carried out essentially as described in Example 5, with five dogs per group. The proteins were administered subcutaneously. Blood glucose concentrations were determined, and are presented in the table below.

TABLE 1

Blood glucose concentrations before and after administration of Humulin ® R, soluble B29-Nε-octanoyl-human insulin ("C8-hI"), or soluble B29-Nε-decanoyl-human insulin ("C10-hI") in normal dogs simultaneously administered somatostatin to create a transient diabetic state. Values are mean ± standard error.

| Time | Blood Glucose Concentration (mg/dL) | | |
|---|---|---|---|
| (h) | Humulin ® R | Soluble C8-hI | Soluble C10-hI |
| −0.5 | 110 ± 2 | 115 ± 4 | 108 ± 2 |
| 0 | 101 ± 2 | 101 ± 7 | 96 ± 4 |
| 0.5 | 83 ± 5 | 80 ± 5 | 85 ± 6 |
| 1 | 54 ± 6 | 52 ± 4 | 70 ± 5 |
| 1.5 | 49 ± 4 | 51 ± 2 | 57 ± 4 |
| 2 | 48 ± 4 | 51 ± 2 | 52 ± 3 |
| 2.5 | 55 ± 4 | 60 ± 3 | 56 ± 4 |
| 3 | 59 ± 2 | 65 ± 4 | 58 ± 4 |
| 3.5 | 65 ± 2 | 73 ± 5 | 63 ± 4 |
| 4 | 71 ± 2 | 85 ± 6 | 68 ± 4 |
| 5 | 87 ± 2 | 110 ± 8 | 79 ± 3 |
| 6 | 104 ± 3 | 124 ± 4 | 91 ± 7 |
| 7 | 119 ± 8 | 145 ± 14 | 106 ± 8 |
| 8 | 144 ± 5 | 153 ± 16 | 119 ± 11 |

These data clearly show that soluble B29-Nε-octanoyl-human insulin and B29-Nε-decanoyl-human insulin, administered subcutaneously to normal dogs in a transient diabetic state, provide glucose lowering roughly comparable to that obtained with soluble human insulin. Most notably, soluble B29-Nε-octanoyl-human insulin shows a quicker onset, and shorter time action than does human insulin.

In a second experiment, the dissolution rate of crystals of B29-Nε-octanoyl-human insulin prepared in accordance with the present invention was found to be markedly longer than that of a commercially manufactured NPH-pork insulin. This was most unexpected in view of the data above. The dissolution rate of the NPH-pork insulin was measured by placing 5 microliters of U100 NPH-pork insulin into 3 mL of Dulbecco's phosphate buffered saline (without calcium or magnesium) in a 1 cm path length square quartz cuvette at a temperature of 22° C. This solution was stirred at a constant rate using a magnetic cuvette stirrer. Absorbance measurements at 320 nm were taken at 1 minute intervals. The absorbance at 320 nm corresponds to the light scattered by the insoluble particles present in the aqueous suspension. Consequently, as the microcrystals dissolve, the absorbance approaches zero. The data generated from this experiment are presented in FIG. 1 as the dashed line, and show that the pork NPH microcrystals were completely dissolved after about 1 hour.

An analogous procedure was followed to measure the dissolution rate of B29-Nε-octanoyl-human insulin microcrystals. A volume of 12 microliters of a suspension of B29-Nε-octanoyl-human insulin microcrystals (containing no more than 50 U/mL), prepared according to the procedure of Preparation 18, was placed into 3 mL of Dulbecco's phosphate buffered saline (without calcium or magnesium) in a 1 cm path length square quartz cuvette. This solution was stirred at the same constant rate and at the same temperature of 22° C. The data generated from this experiment are presented in FIG. 1 as the solid line, and show that the B29-Nε-octanoyl-human insulin microcrystals required much more than 5 hours to dissolve.

These experiments establish that, in Dulbecco's phosphate buffered saline (without calcium and magnesium), a solution that mimics the interstitial fluid in certain aspects, the rate of dissolution of the B29-Nε-octanoyl-human insulin microcrystals is significantly slower than that of pork NPH microcrystals. Again, this finding was very surprising in light of the previous finding that soluble B29-Nε-octanoyl-human insulin had a time action actually slightly shorter than did human insulin!

Subcutaneous interstitial fluid contains 0.3 mM human serum albumin. Therefore, another experiment was designed to compare the dissolution rates of approximately equal quantities of B29-Nε-octanoyl-human insulin microcrystals and pork NPH microcrystals in Dulbecco's phosphate buffered saline containing 0.3 mM human serum albumin.

This experiment was performed by placing 25 microliters of NPH pork insulin (approximately 3.5 mg insulin/mL) into 2 mL of Dulbecco's phosphate buffered saline (without calcium and magnesium) containing 0.3 mM human serum albumin. The resulting suspension was swirled gently by hand whereupon the microcrystals were observed to be dissolved after about 3 to 5 minutes.

The rate of dissolution of B29-Nε-octanoyl-human insulin microcrystals was observed by placing 50 microliters of a B29-Nε-octanoyl-human insulin microcrystalline formulation (approximately 1.8 mg/mL), prepared essentially as described in Preparation 18 herein, into 2 mL of Dulbecco's phosphate buffered saline (without calcium and magnesium) containing 0.3 mM human serum albumin. The resulting suspension was swirled gently by hand for about 3 to 5 minutes whereupon minimal dissolution of the suspended microcrystals was observed to have taken place. Continued gentle stirring of this solution using a magnetic stirrer resulted in complete dissolution of the suspended B29-Nε-octanoyl-human insulin microcrystals after about 2 hours.

These experiments establish that the rate of dissolution of the B29-Nε-octanoyl-human insulin microcrystals is significantly slower than the rate of dissolution of commercially manufactured pork NPH microcrystals in Dulbecco's phosphate buffered saline (without calcium and magnesium) containing 0.3 mM human serum albumin.

Because the time action profile of NPH insulin preparations is related strongly to the rate of dissolution of the microcrystals in the subcutaneous interstitial fluid, it is concluded from these experiments that the B29-Nε-octanoyl-human insulin microcrystalline suspension formulation will possess a more protracted duration of action when administered subcutaneously to diabetic patients than existing commercial NPH insulin preparations.

The insoluble compositions of the present invention may be crystals with rod-like morphology or with an irregular morphology, or they may be amorphous precipitates. Preferred insoluble compositions are comprised of acylated insulin or acylated insulin analog, zinc ions, which are present at about 0.3 to about 0.7 mole per mole of derivatized protein, a phenolic preservative selected from the group consisting of phenol, m-cresol, o-cresol, p-cresol, chlorocresol, methylparaben, and mixtures thereof and is present in sufficient proportions with respect to the derivatized protein to facilitate formation of the R6 hexamer conformation, and protamine, which is present at about 0.15 to about 0.7 mole per mole of derivatized protein.

The preferred derivatized proteins are acylated proteins, and the preferred acylated proteins for the microcrystals and formulations of the present invention are fatty acid-acylated insulin, and fatty acid-acylated insulin analogs. Fatty acid-acylated human insulin is highly preferred. Fatty acid-acylated insulin analogs are equally highly preferred.

A preferred group of insulin analogs for preparing acylated insulin analogs used to form the microcrystals of the present invention consists of insulin analogs wherein the amino acid residue at position B28 is Asp, Lys, Leu, Val, or Ala, the amino acid residue at position B29 is Lys or Pro, the amino acid residue at position B10 is His or Asp, the amino acid residue at position B1 is Phe, Asp or deleted alone or in combination with a deletion of the residue at position B2, the amino acid residue at position B30 is Thr, Ala, Ser, or deleted, and the amino acid residue at position B9 is Ser or Asp; provided that either position B28 or B29 is Lys.

Another preferred group of insulin analogs for use in the present invention consists of those wherein the isoelectric point of the insulin analog is between about 7.0 and about 8.0. These analogs are referred to as "pi-shifted insulin analogs." Examples of pi-shifted insulin analogs include, for example, ArgB31,ArgB32-human insulin, GlyA21,ArgB31, ArgB32-human insulin, ArgA0,ArgB31,ArgB32-human insulin, and ArgA0,GlyA21,ArgB31,ArgB32-human insulin.

Another preferred group of insulin analogs consists of LysB28,ProB29-human insulin (B28 is Lys; B29 is Pro); AspB28-human insulin (B28 is Asp), AspB1-human insulin, ArgB31,ArgB32-human insulin, ArgA0-human insulin, AspB1,GluB13-human insulin, AlaB26-human insulin, GlyA21-human insulin, des(ThrB30)-human insulin, and GlyA21,ArgB31,ArgB32-human insulin.

Especially preferred insulin analogs include LysB28, ProB29-human insulin, des(ThrB30)-human insulin, AspB28-human insulin, and AlaB26-human insulin. Another especially preferred insulin analog is GlyA21, ArgB31, ArgB32-human insulin [Dörschug, M., U.S. Pat. No. 5,656,722, Aug. 12, 1997]. The most preferred insulin analog is LysB28,ProB29-human insulin.

One preferred group of acylating moieties consists of fatty acids that are straight chain and saturated. This group consists of methanoic acid (C1), ethanoic acid (C2), propanoic acid (C3), n-butanoic acid (C4), n-pentanoic acid (C5), n-hexanoic acid (C6), n-heptanoic acid (C7), n-octanoic acid (C8), n-nonanoic acid (C9), n-decanoic acid (C10), n-undecanoic acid (C11), n-dodecanoic acid (C12), n-tridecanoic acid (C13), n-tetradecanoic acid (C14), n-pentadecanoic acid (C15), n-hexadecanoic acid (C16), n-heptadecanoic acid (C17), and n-octadecanoic acid (C18). Adjectival forms are formyl (C1), acetyl (C2), propionyl (C3), butyryl (C4), pentanoyl (C5), hexanoyl (C6), heptanoyl (C7), octanoyl (C8), nonanoyl (C9), decanoyl (C10), undecanoyl (C11), dodecanoyl (C12), tridecanoyl (C13), tetradecanoyl (C14) or myristoyl, pentadecanoyl (C15), hexadecanoyl (C16) or palmitic, heptadecanoyl (C17), and octadecanoyl (C18).

A preferred group of fatty acids for forming the fatty acid-acylated proteins used in the microcrystals of the present invention consists of fatty acids having an even number of carbon atoms—that is, C2, C4, C6, C8, C10, C12, C14, C16, and C18 saturated fatty acids.

Another preferred group of fatty acids for forming the fatty acid-acylated proteins used in the microcrystals of the present invention consists of fatty acids having an odd number of carbon atoms—that is, C1, C3, C5, C7, C9, C11, C13, C15, and C17 saturated fatty acids.

Another preferred group of fatty acids for forming the fatty acid-acylated proteins used in the microcrystals of the present invention consists of fatty acids having more than 5 carbon atoms—that is, C6, C7, C8, C9, C10, C11, C12, C13, C14, C15, C16, C17, and C18 saturated fatty acids.

Another preferred group of fatty acids for forming the fatty acid-acylated proteins used in the microcrystals of the present invention consists of fatty acids having less than 9 carbon atoms—that is, C1, C2, C3, C4, C5, C6, C7, and C8 saturated fatty acids.

Another preferred group of fatty acids for forming the fatty acid-acylated proteins used in the microcrystals of the present invention consists of fatty acids having between 6 and 8 carbon atoms—that is, C6, C7, and C8, saturated fatty acids.

Another preferred group of fatty acids for forming the fatty acid-acylated proteins used in the microcrystals of the present invention consists of fatty acids having more than between 4 and 6 carbon atoms—that is, C4, C5, and C6, saturated fatty acids.

Another preferred group of fatty acids for forming the fatty acid-acylated proteins used in the microcrystals of the present invention consists of fatty acids having more than between 2 and 4 carbon atoms—that is, C2, C3, and C4, saturated fatty acids.

Another preferred group of fatty acids for forming the fatty acid-acylated proteins used in the microcrystals of the present invention consists of fatty acids having less than 6 carbon atoms—that is, C1, C2, C3, C4, and C5 saturated fatty acids.

Another preferred group of fatty acids for forming the fatty acid-acylated proteins used in the microcrystals of the present invention consists of fatty acids having less than 4 carbon atoms—that is, C1, C2, and C3 saturated fatty acids.

Another preferred group of fatty acids for forming the fatty acid-acylated proteins used in the microcrystals of the present invention consists of fatty acids having more than 9 carbon atoms—that is, C10, C11, C12, C13, C14, C15, C16, C17, and C18 saturated fatty acids.

Another preferred group of fatty acids for forming the fatty acid-acylated proteins used in the microcrystals of the present invention consists of fatty acids having an even number of carbon atoms and more than 9 carbon atoms—that is, C10, C12, C14, C16, and C18 saturated fatty acids.

Another preferred group of fatty acids for forming the fatty acid-acylated proteins used in the microcrystals of the present invention consists of fatty acids having 12, 14, or 16 carbon atoms, that is, C12, C14, and C16 saturated fatty acids.

Another preferred group of fatty acids for forming the fatty acid-acylated proteins used in the microcrystals of the present invention consists of fatty acids having 14 or 16 carbon atoms, that is, C14 and C16 saturated fatty acids. Fatty acids with 14 carbons are particularly preferred. Fatty acids with 16 carbons are also particularly preferred.

Another preferred group of fatty acids for forming the fatty acid-acylated proteins used in the microcrystals of the present invention consists of saturated fatty acids having between 4 and 10 carbon atoms, that is C4, C5, C6, C7, C8, C9, and C10 saturated fatty acids.

Another preferred group of fatty acids for forming the fatty acid-acylated proteins used in the microcrystals of the present invention consists of saturated fatty acids having an even number of carbon atoms between 4 and 10 carbon atoms, that is C4, C6, C8, and C10 saturated fatty acids.

Another preferred group of fatty acids for forming the fatty acid-acylated proteins used in the microcrystals of the present invention consists of fatty acids having between 6, 8, or 10 carbon atoms. Fatty acids with 6 carbons are particularly preferred. Fatty acids with 8 carbons are also particularly preferred. Fatty acids with 10 carbons are particularly preferred.

The skilled person will appreciate that narrower preferred groups are made by combining the preferred groups of fatty acids described above.

Another preferred group of acylating moieties consists of saturated fatty acids that are branched. A branched fatty acid has at least two branches. The length of a "branch" of a branched fatty acid may be described by the number of carbon atoms in the branch, beginning with the acid carbon. For example, the branched fatty acid 3-ethyl-5-methylhexanoic acid has three branches that are five, six, and six carbons in length. In this case, the "longest" branch is six carbons. As another example, 2,3,4,5-tetraethyloctanoic acid has five branches that are 4, 5, 6, 7, and 8 carbons long. The "longest" branch is eight carbons. A preferred group of branched fatty acids are those having from three to ten carbon atoms in the longest branch.

A representative number of such branched, saturated fatty acids will be mentioned to assure the reader's comprehension of the range of such fatty acids that may be used as acylating moieties of the proteins in the present invention: 2-methyl-propioinic acid, 2-methyl-butyric acid, 3-methyl-butyric acid, 2,2-dimethyl-propionic acid, 2-methyl-pentanoic acid, 3-methyl-pentanoic acid, 4-methyl-pentanoic acid, 2,2-dimethyl-butyric acid, 2,3-dimethyl-butyric acid, 3,3-dimethyl-butyric acid, 2-ethyl-butyric acid, 2-methyl-hexanoic acid, 5-methyl-hexanoic acid, 2,2-dimethyl-pentanoic acid, 2,4-dimethyl-pentanoic acid, 2-ethyl-3-methyl-butyric acid, 2-ethyl-pentanoic acid, 3-ethyl-pentanoic acid, 2,2-dimethyl-3-methyl-butyric acid, 2-methyl-heptanoic acid, 3-methyl-heptanoic acid, 4-methyl-heptanoic acid, 5-methyl-heptanoic acid, 6-methyl-heptanoic acid, 2,2-dimethyl-hexanoic acid, 2,3-dimethyl-hexanoic acid, 2,4-dimethyl-hexanoic acid, 2,5-dimethyl-hexanoic acid, 3,3,-dimethyl-hexanoic acid, 3,4-dimethyl-hexanoic acid, 3,5-dimethyl-hexanoic acid, 4,4-dimethyl-hexanoic acid, 2-ethyl-hexanoic acid, 3-ethyl-hexanoic acid, 4-ethyl-hexanoic acid, 2-propyl-pentanoic acid, 2-ethyl-hexanoic acid, 3-ethyl-hexanoic acid, 4-ethyl-hexanoic acid, 2-(1-propyl)pentanoic acid, 2-(2-propyl)pentanoic acid, 2,2-diethyl-butyric acid, 2,3,4-trimethyl-pentanoic acid, 2-methyl-octanoic acid, 4-methyl-octanoic acid, 7-methyl-octanoic acid, 2,2-dimethyl-heptanoic acid, 2,6-dimethyl-heptanoic acid, 2-ethyl-2-methyl-hexanoic acid, 3-ethyl-5-methyl-hexanoic acid, 3-(1-propyl)-hexanoic acid, 2-(2-butyl)-pentanoic acid, 2-(2-(2-methylpropyl))pentanoic acid,2-methyl-nonanoic acid, 8-methyl-nonanoic acid, 6-ethyl-octanoic acid, 4-(1-propyl)-heptanoic acid, 5-(2-propyl)-heptanoic acid,3-methyl-undecanoic acid,2-pentyl-heptanoic acid, 2,3,4,5,6-pentamethyl-heptanoic acid, 2,6-diethyl-octanoic acid, 2-hexyl-octanoic acid, 2,3,4,5,6,7-hexamethyl-octanoic acid, 3,3-diethyl-4,4-diethyl-hexanoic acid, 2-heptyl-nonanoic acid, 2,3,4,5-tetraethyl-octanoic acid, 2-octyl-decanoic acid, and 2-(1-propyl)-3-(1-propyl)-4,5-diethyl-6-methyl-heptanoic acid.

Yet another preferred group of acylating moieties consists of cyclic alkyl acids having from 5 to 24 carbon atoms, wherein the cyclic alkyl moiety, or moieties, have 5 to 7 carbon atoms. A representative number of such cyclic alkyl acids will be mentioned to assure the reader's comprehension of the range of such acids that may be used as acylating moieties of the proteins in the present invention: cyclopentyl-formic acid, cyclohexyl-formic acid, 1-cyclopentyl-acetic acid, 2-cyclohexyl-acetic acid, 1,2-dicyclopentyl-acetic acid, and the like.

A preferred group of derivatized proteins for use in the microcrystals of the present invention consists of mono-acylated proteins. Mono-acylation at the $\epsilon$-amino group is most preferred. For insulin, mono-acylation at LysB29 is preferred. Similarly, for certain insulin analogs, such as, LysB28,ProB29-human insulin analog, mono-acylation at the $\epsilon$-amino group of LysB28 is most preferred. Mono-acylation at the $\alpha$-amino group of the B-chain (B1) is also preferred. Mono-acylation at the $\alpha$-amino group of the A-chain (A1) is also preferred.

Another preferred group of acylated proteins for use in the microcrystals of the present invention consists of di-acylated proteins. The di-acylation may be, for example, at the $\epsilon$-amino group of Lys and at the $\alpha$-amino group of the B-chain, or may be at the $\epsilon$-amino group of Lys and at the $\alpha$-amino group of the A-chain, or may be at the $\alpha$-amino group the A-chain and at the $\alpha$-amino group of the B-chain.

Another preferred group of acylated proteins for use in the microcrystals of the present invention consists of tri-acylated proteins. Tri-acylated proteins are those that are acylated at the $\epsilon$-amino group of Lys, at the $\alpha$-amino group of the B-chain, and at the $\alpha$-amino group of the A-chain.

It is also preferred to use acylated proteins that are a mixture of mono-acylated and di-acylated proteins.

It is likewise preferred to use acylated proteins that are a mixture of mono-acylated and tri-acylated proteins.

Another preferred group of acylated proteins consists of a mixture of di-acylated and tri-acylated proteins.

Also preferred is to use acylated proteins that are a mixture of mono-acylated, di-acylated, and tri-acylated proteins.

Certain fatty acid-acylated proteins used in the present microcrystals will be mentioned to assure the reader's comprehension of the scope of the present invention. The list is illustrative, and the fact that a particular fatty acid-acylated protein is not mentioned does not mean that a microcrystal containing it is not within the scope of the present invention.

B29-N$\epsilon$-Formyl-human insulin.
B1-N$\alpha$-Formyl-human insulin.
A1-N$\alpha$-Formyl-human insulin.
B29-N$\epsilon$-Formyl-,B1-N$\alpha$-formyl-human insulin.
B29-N$\epsilon$-Formyl-, A1-N$\alpha$-formyl-human insulin.
A1-N$\alpha$-Formyl-,B1-N$\alpha$-formyl-human insulin.
B29-N$\epsilon$-Formyl-, A1-N$\alpha$-formyl-, B1-N$\alpha$-formyl-human insulin.
B2 9-N$\epsilon$-Acetyl -human insulin.
B1-N$\alpha$-Acetyl-human insulin.
A1-N$\alpha$-Acetyl -human insulin.
B29-N$\epsilon$-Acetyl-, B1-N$\alpha$-acetyl-human insulin.

B29-Nε-Acetyl-, A1-Nα-acetyl-human insulin.
A1-Nα-Acetyl-, B1-Nα-acetyl-human insulin.
B29-Nε-Acetyl-, A1-Nα-acetyl-, B1-Nα-acetyl-human insulin.
B29-Nε-Propionyl-human insulin.
B1-Nα-Propionyl-human insulin.
A1-Nα-Propionyl-human insulin.
B29-Nε-Propionyl-,B1-Nα-propionyl-human insulin.
B29-Nε-Propionyl-,A1-Nα-propionyl-human insulin.
A1-Nα-Propionyl-,B1-Nα-propionyl-human insulin.
B29-Nε-Propionyl-, A1-Nα-propionyl-, B1-Nα-propionyl-human insulin.
B29-Nε-Butyryl-human insulin.
B1-Nα-Butyryl-human insulin.
A1-Nα-Butyryl-human insulin.
B29-Nε-Butyryl-,B1-Nα-butyryl-human insulin.
B29-Nε-Butyryl-,A1-Nα-butyryl-human insulin.
A1-Nα-Butyryl-,B1-Nα-butyryl-human insulin.
B29-Nε-Butyryl-, A1-Nα-butyryl-,B1-Nα-butyryl-human insulin.
B29-Nε-Pentanoyl-human insulin.
B1-Nα-Pentanoyl-human insulin.
A1-Nα-Pentanoyl-human insulin.
B29-Nε-Pentanoyl-,B1-Nα-pentanoyl-human insulin.
B29-Nε-Pentanoyl-,A1-Nα-pentanoyl-human insulin.
A1-Nα-Pentanoyl-,B1-Nα-pentanoyl-human insulin.
B29-Nε-Pentanoyl-, A1-Nα-pentanoyl-,B1-Nα-pentanoyl-human insulin.
B29Nε-Hexanoyl-human insulin.
B1 -Nα-Hexanoyl-human insulin.
A1-Nα-Hexanoyl-human insulin.
B29-Nε-Hexanoyl-,B1-Nα-hexanoyl-human insulin.
B29-Nε-Hexanoyl-,A1-Nα-hexanoyl-human insulin.
A1-Nα-Hexanoyl-,B1-Nα-hexanoyl-human insulin.
B29-Nε-Hexanoyl-, A1-Nα-hexanoyl-,B1-Nα-hexanoyl-human insulin.
B29-Nε-Heptanoyl-human insulin.
B1-Nα-Heptanoyl-human insulin.
A1-Nα-Heptanoyl-human insulin.
B29-Nε-Heptanoyl-,B1-Nα-heptanoyl-human insulin.
B29-Nε-Heptanoyl-,A1-Nα-heptanoyl-human insulin.
A1-Nα-Heptanoyl-,B1-Nα-heptanoyl-human insulin.
B29-Nε-Heptanoyl-, A1-Nα-heptanoyl-,B1-Nα-heptanoyl-human insulin.
B29-Nε-Octanoyl-human insulin.
B1-Nα-Octanoyl-human insulin.
A1-Nα-Octanoyl-human insulin.
B29-Nε-Octanoyl-,B1-Nα-octanoyl-human insulin.
B29-Nε-Octanoyl-,A1-Nα-octanoyl-human insulin.
A1-Nα-Octanoyl-,B1-Nα-octanoyl-human insulin.
B29-Nε-Octanoyl-, A1-Nα-octanoyl-,B1-Nα-octanoyl-human insulin.
B29-Nε-Nonanoyl-human insulin.
B1-Nα-Nonanoyl-human insulin.
A1-Nα-Nonanoyl-human insulin.
B29-Nε-Nonanoyl-,B1-Nα-nonanoyl-human insulin.
B29-Nε-Nonanoyl-,A1-Nα-nonanoyl-human insulin.
A1-Nα-Nonanoyl-,B1-Nα-nonanoyl-human insulin.
B29-Nε-Nonanoyl-, A1-Nα-nonanoyl-,B1-Nα-nonanoyl-human insulin.
B29-Nε-Decanoyl-human insulin.
B1-Nα-Decanoyl-human insulin.
A1-Nα-Decanoyl-human insulin.
B29-Nε-Decanoyl-,B1-Nα-decanoyl-human insulin.
B29-Nε-Decanoyl-,A1-Nα-decanoyl-human insulin.
A1-Nα-Decanoyl-,B1-Nα-decanoyl-human insulin.
B29-Nε-Decanoyl-,A1-Nα-decanoyl- ,B1-Nα-decanoyl-human insulin.

B28-Nε-Formyl-LysB28,ProB29-human insulin analog.
B1-Nα-Formyl-LysB28,ProB29-human insulin analog.
A1-Nα-Formyl-LysB28,ProB29-human insulin analog.
B28-Nε-Formyl-,B1-Nα-formyl-LysB28,ProB29-human insulin analog.
B28-Nε-Formyl-, A1-Nα-formyl-LysB28,ProB29-human insulin analog.
A1-Nα-Formyl-,B1-Nα-formyl-LysB28,ProB29-human insulin analog.
B28-Nε-Formyl-, A1-Nα-formyl-, B1-Nα-formyl-LysB28,ProB29-human insulin analog.
B28-Nε-Acetyl-LysB28,ProB29-human insulin analog.
B1-Nα-Acetyl-LysB28,ProB29-human insulin analog.
A1-Nα-Acetyl-LysB28,ProB29-human insulin analog.
B28-Nε-Acetyl-, B1-Nα-acetyl-LysB28,ProB29-human insulin analog.
B28-Nε-Acetyl-, A1-Nα-acetyl-LysB28,ProB29-human insulin analog.
A1-Nα-Acetyl-, B1-Nα-acetyl-LysB28,ProB29-human insulin analog.
B28-Nε-Acetyl-, A1-Nα-acetyl-, B1-Nα-acetyl-LysB28,ProB29-human insulin analog.
B28-Nε-Propionyl-LysB28,ProB29-human insulin analog.
B1-Nα-Propionyl-LysB28,ProB29-human insulin analog.
A1-Nα-Propionyl-LysB28,ProB29-human insulin analog.
B28-Nε-Propionyl-, B1-Nα-propionyl-LysB28, ProB29-human insulin analog.
B28-Nε-Propionyl-,A1-Nα-propionyl-LysB28, ProB29-human insulin analog.
A1-Nα-Propionyl-,B1-Nα-propionyl-LysB28,ProB29-human insulin analog.
B28-Nε-Propionyl-, A1-Nα-propionyl-, B1-Nα-propionyl-LysB28,ProB29-human insulin analog.
B28-Nε-Butyryl-LysB28,ProB29-human insulin analog.
B1-Nα-Butyryl-LysB28,ProB29-human insulin analog.
A1-Nα-Butyryl-LysB28,ProB29-human insulin analog.
B28-Nε-Butyryl-,B1-Nα-butyryl-LysB28,ProB29-human insulin analog.
B28-Nε-Butyryl-,A1-Nα-butyryl-LysB28,ProB29-human insulin analog.
A1-Nα-Butyryl-,B1-Nα-butyryl-LysB28,ProB29-human insulin analog.
B28-Nε-Butyryl-, A1-Nα-butyryl-, B1-Nα-butyryl-LysB28,ProB29-human insulin analog.
B28-Nε-Pentanoyl-LysB28,ProB29-human insulin analog.
B1-Nα-Pentanoyl-LysB28,ProB29-human insulin analog.
A1-Nα-Pentanoyl-LysB28,ProB29-human insulin analog.
B28-Nε-Pentanoyl-, B1-Nα-pentanoyl-LysB28, ProB29-human insulin analog.
B28-Nε-Pentanoyl-,A1-Nα-pentanoyl-LysB28,ProB29-human insulin analog.
A1-Nα-Pentanoyl-,B1-Nα-pentanoyl-LysB28,ProB29-human insulin analog.
B28-Nε-Pentanoyl-, A1-Nα-pentanoyl-,B1-Nα-pentanoyl-LysB28,ProB29-human insulin analog.
B28-Nε-Hexanoyl-LysB28,ProB29-human insulin analog.
B1-Nα-Hexanoyl-LysB28,ProB29-human insulin analog.
A1-Nα-Hexanoyl-LysB28,ProB29-human insulin analog.
B28-Nε-Hexanoyl-,B1-Nα-hexanoyl-LysB28,ProB29-human insulin analog.
B28-Nε-Hexanoyl-,A1-Nα-hexanoyl-LysB28,ProB29-human insulin analog.
A1-Nα-Hexanoyl-,B1-Nα-hexanoyl-LysB28,ProB29-human insulin analog.
B28-Nε-Hexanoyl-, A1-Nα-hexanoyl-,B1-Nα-hexanoyl-LysB28,ProB29-human insulin analog.
B28-Nε-Heptanoyl-LysB28,ProB29-human insulin analog.

B1-Nα-Heptanoyl-LysB28,ProB29-human insulin analog.
A1-Nα-Heptanoyl-LysB28,ProB29-human insulin analog.
B28-Nε-Heptanoyl-, B1-Nα-heptanoyl-LysB28, ProB29-human insulin analog.
B28-Nε-Heptanoyl-, A1-Nα-heptanoyl-LysB28, ProB29-human insulin analog.
A1-Nα-Heptanoyl-,B1-Nα-heptanoyl-LysB28,ProB29-human insulin analog.
B28-Nε-Heptanoyl-, A1-Nα-heptanoyl-,B1-Nα-heptanoyl-LysB28,ProB29-human insulin analog.
B28-Nε-Octanoyl-LysB28,ProB29-human insulin analog.
B1-Nα-Octanoyl-LysB28,ProB29-human insulin analog.
A1-Nα-Octanoyl-LysB28,ProB29-human insulin analog.
B28-Nε-Octanoyl-,B1-Nα-octanoyl-LysB28,ProB29-human insulin analog.
B28-Nε-Octanoyl-,A1-Nα-octanoyl-LysB28,ProB29-human insulin analog.
A1-Nα-Octanoyl-,B1-Nα-octanoyl-LysB28,ProB29-human insulin analog.
B28-Nε-Octanoyl-, A1-Nα-octanoyl-,B1-Nα-octanoyl-LysB28,ProB29-human insulin analog.
B28-Nε-Nonanoyl-LysB28,ProB29-human insulin analog.
B1-Nα-Nonanoyl-LysB28,ProB29-human insulin analog.
A1-Nα-Nonanoyl-LysB28,ProB29-human insulin analog.
B28-Nε-Nonanoyl-,B1-Nα-nonanoyl-LysB28,ProB29-human insulin analog.
B28-Nε-Nonanoyl-,A1-Nα-nonanoyl-LysB28,ProB29-human insulin analog.
A1-Nα-Nonanoyl-,B1-Nα-nonanoyl-LysB28,ProB29-human insulin analog.
B28-Nε-Nonanoyl-, A1-Nα-nonanoyl-,B1-Nα-nonanoyl-LysB28,ProB29-human insulin analog.
B28-Nε-Decanoyl-LysB28,ProB29-human insulin analog.
B1-Nα-Decanoyl-LysB28,ProB29-human insulin analog.
A1-Nα-Decanoyl-LysB28,ProB29-human insulin analog.
B28-Nε-Decanoyl-,B1-Nα-decanoyl-LysB28,ProB29-human insulin analog.
B28-Nε-Decanoyl-,A1-Nα-decanoyl-LysB28,ProB29-human insulin analog.
A1-Nα-Decanoyl-,B1-Nα-decanoyl-LysB28,ProB29-human insulin analog.
B28-Nε-Decanoyl-,A1-Nα-decanoyl-,B1-Nα-decanoyl-LysB28,ProB29-human insulin analog.
B29-Nε-Pentanoyl-GlyA21,ArgB31,ArgB32-human insulin.
B1-Nα-Hexanoyl-GlyA21,ArgB31,ArgB32-human insulin.
A1-Nα-Heptanoyl-GlyA21,ArgB31,ArgB32-human insulin.
B29-Nε-Octanoyl-,B1-Nα-octanoyl-GlyA21,ArgB31,ArgB32-human insulin.
B29-Nε-Propionyl-, A1-Nα-propionyl-GlyA21,ArgB31,ArgB32-human insulin.
A1-Nα-Acetyl, B1-Nα-acetyl-GlyA21,ArgB31,ArgB32-human insulin.
B29-Nε-Formyl-, A1-Nα-formyl-,B1-Nα-formyl-GlyA21,ArgB31,ArgB32-human insulin.
B29-Nε-Formyl-des(TyrB26)-human insulin.
B1-Nα-Acetyl-AspB28-human insulin.
B29-Nε-Propionyl-, A1-Nα-propionyl-,B1-Nα-propionyl-AspB1,AspB3,AspB21-human insulin.
B29-Nε-Pentanoyl-GlyA21-human insulin.
B1-Nα-Hexanoyl-GlyA21-human insulin.
A1-Nα-Heptanoyl-GlyA21-human insulin.
B29-Nε-Octanoyl-,B1-Nα-octanoyl-GlyA21-human insulin.
B29-Nε-Propionyl-, A1-Nα-propionyl-GlyA21-human insulin.
A1-Nα-Acetyl, B1-Nα-acetyl-GlyA21-human insulin.
B29-Nε-Formyl-, A1-Nα-formyl-,B1-Nα-formyl-GlyA21-human insulin.
B29-Nε-Butyryl-des(ThrB30)-human insulin.
B1-Nα-Butyryl-des(ThrB30)-human insulin.
A1-Nα-Butyryl-des(ThrB30)-human insulin.
B29-Nε-Butyryl-,B1-Nα-butyryl-des(ThrB30)-human insulin.
B29-Nε-Butyryl-,A1-Nα-butyryl-des(ThrB30)-human insulin.
A1-Nα-Butyryl-,B1-Nα-butyryl-des(ThrB30)-human insulin.
B29-Nε-Butyryl-,A1-Nα-butyryl-,B1-Nα-butyryl-des(ThrB30)-human insulin.

Aqueous compositions containing water as the major solvent are preferred. Aqueous suspensions wherein water is the solvent are highly preferred.

The compositions of the present invention are used to treat patients who have diabetes or hyperglycemia. The formulations of the present invention will typically provide derivatized protein at concentrations of from about 1 mg/mL to about 10 mg/mL. Present formulations of insulin products are typically characterized in terms of the concentration of units of insulin activity (units/mL), such as U40, U50, U100, and so on, which correspond roughly to about 1.4, 1.75, and 3.5 mg/mL preparations, respectively. The dose, route of administration, and the number of administrations per day will be determined by a physician considering such factors as the therapeutic objectives, the nature and cause of the patient's disease, the patient's gender and weight, level of exercise, eating habits, the method of administration, and other factors known to the skilled physician. In broad range, a daily dose would be in the range of from about 1 nmol/kg body weight to about 6 nmol/kg body weight (6 nmol is considered equivalent to about 1 unit of insulin activity). A dose of between about 2 and about 3 nmol/kg is typical of present insulin therapy.

The physician of ordinary skill in treating diabetes will be able to select the therapeutically most advantageous means to administer the formulations of the present invention. Parenteral routes of administration are preferred. Typical routes of parenteral administration of suspension formulations of insulin are the subcutaneous and intramuscular routes. The compositions and formulations of the present invention may also be administered by nasal, buccal, pulmonary, or occular routes.

Glycerol at a concentration of 12 mg/mL to 25 mg/mL is preferred as an isotonicity agent. Yet more highly preferred for isotonicity is to use glycerol at a concentration of from about 15 mg/mL to about 17 mg/mL.

M-cresol and phenol, or mixtures thereof, are preferred preservatives in formulations of the present invention.

Insulin, insulin analogs, or proinsulins used to prepare derivatized proteins can be prepared by any of a variety of recognized peptide synthesis techniques including classical (solution) methods, solid phase methods, semi-synthetic methods, and more recent recombinant DNA methods. For example, see Chance, R. E., et al., U.S. Pat. No. 5,514,646, May 7, 1996; EPO publication number 383,472, Feb. 7, 1996; Brange, J. J. V., et al. EPO publication number 214,826, Mar. 18, 1987; and Belagaje, R. M., et al., U.S. Pat. No. 5,304,473, Apr. 19, 1994, which disclose the preparation of various proinsulin and insulin analogs. These references are expressly incorporated herein by reference.

Generally, derivatized proteins are prepared using methods known in the art. The publications listed above to describe derivatized proteins contain suitable methods to prepare derivatized proteins. Those publications are expressly incorporated by reference for methods of preparing derivatized proteins. To prepare acylated proteins, the protein is reacted with an activated organic acid, such as an activated fatty acid. Activated fatty acids are derivatives of commonly employed acylating agents, and include activated esters of fatty acids, fatty acid halides, activated amides of fatty acids, such as, activated azolide derivatives [Hansen, L. B., WIPO Publication No. 98/02460, Jan. 22, 1998], and fatty acid anhydrides. The use of activated esters, especially N-hydroxysuccinimide esters of fatty acids, is a particularly advantageous means of acylating a free amino acid with a fatty acid. Lapidot, et al. describe the preparation of N-hydroxysuccinimide esters and their use in the preparation of N-lauroyl-glycine, N-lauroyl-L-serine, and N-lauroyl-L-glutamic acid. The term "activated fatty acid ester" means a fatty acid which has been activated using general techniques known in the art [Riordan, J. F. and Vallee, B. L., *Methods in Enzymology*, XXV:494–499 (1972); Lapidot, Y., et al., *J. Lipid Res.* 8:142–145 (1967)]. Hydroxybenzotriazide (HOBT), N-hydroxysuccinimide and derivatives thereof are particularly well known for forming activated acids for peptide synthesis.

To selectively acylate the ε-amino group, various protecting groups may be used to block the α-amino groups during the coupling. The selection of a suitable protecting group is known to one skilled in the art and includes p-methoxybenzoxycarbonyl (pmZ). Preferably, the ε-amino group is acylated in a one-step synthesis without the use of amino-protecting groups. A process for selective acylation at the Nε-amino group of Lys is disclosed and claimed by Baker, J. C., et al., U.S. Pat. No. 5,646,242, Jul. 8, 1997, the entire disclosure of which is incorporated expressly by reference. A process for preparing a dry powder of an acylated protein is disclosed and claimed by Baker, J. C., et al., U.S. Pat. No. 5,700,904, Dec. 23, 1997, the entire disclosure of which is incorporated herein expressly by reference.

The primary role of zinc in the present invention is to facilitate formation of Zn(II) hexamers of the derivatized protein. Zinc is known to facilitate the formation of hexamers of insulin, and of insulin analogs. Zinc likewise promotes the formation of hexamers of derivatized insulin and insulin analogs. Hexamer formation is conveniently achieved by bringing the pH of a solution comprising derivatized protein into the neutral region in the presence of Zn(II) ions, or by adding Zn(II) after the pH has been adjusted to the neutral region.

For efficient yield of microcrystals or amorphous precipitate, the ratio of zinc to derivatized protein in the microcrystal and amorphous precipitate of the present invention is bounded at the lower limit by about 0.33, that is, two zinc atoms per hexamer of derivatized protein which are needed for efficient hexamerization. The microcrystal and amorphous precipitate compositions will form suitably with about 2 to about 4–6 zinc atoms present. Even more zinc may be used during the process if a compound that competes with the protein for zinc binding, such as citrate or phosphate, is present. Excess zinc above the amount needed for hexamerization may be desirable to more strongly drive hexamerization. Also, excess zinc above the amount needed for hexamerization can be present in a formulation of the present invention, and may be desirable to improve chemical and physical stability, to improve suspendability, and possibly to extend time-action further. Consequently there is a fairly wide range of zinc:protein ratios allowable in the formulations of the present invention.

In accordance with the present invention, zinc is present in the formulation in an amount of from about 0.3 mole to about 7 moles per mole of derivatized protein and more preferably about from 0.3 mole to about 1.0 mole of derivatized protein. Yet more highly preferred is a ratio of zinc to derivatized protein from about 0.3 to about 0.7 mole of zinc atoms per mole of derivatized protein. Most highly preferred is a ratio of zinc to derivatized protein from about 0.30 to about 0.55 mole of zinc atoms per mole of derivatized protein. For higher zinc formulations that are similar to PZI preparations, the zinc ratio is from about 5 to about 7 moles of zinc per mole of derivatized protein.

The zinc compound that provides zinc for the present invention may be any pharmaceutically acceptable zinc compound. The addition of zinc to insulin preparations is known in the art, as are pharmaceutically acceptable sources of zinc. Preferred zinc compounds to supply zinc for the present invention include zinc chloride, zinc acetate, zinc citrate, zinc oxide, and zinc nitrate.

A complexing compound is required for the microcrystals and precipitates of the present invention. The complexing compound must be present in sufficient quantities to cause substantial precipitation and crystallization of hexamers of the derivatized protein. Such quantities can be readily determined for a particular preparation of a particular complexing compound by simple titration experiments. Ideally, the complexing compound concentration is adjusted so that there is negligible complexing compound remaining in the soluble phase after completion of precipitation and crystallization. This requires combining the complexing compound based on an experimentally determined "isophane" ratio. This ratio is expected to be very similar to that of NPH and NPL. However, it may be slightly different because acylation may affect the nature of the protein-protamine interaction.

When protamine is the complexing compound, it is present in the microcrystal in an amount of from about 0.15 mg to about 0.5 mg per 3.5 mg of the derivatized protein. The ratio of protamine to derivatized protein is preferably from about 0.25 to about 0.40 (mg/mg). More preferably the ratio is from about 0.25 to about 0.38 (mg/mg). Preferably, protamine is in an amount of 0.05 mg to about 0.2 mg per mg of the derivatized protein, and more preferably, from about 0.05 to about 0.15 milligram of protamine per milligram of derivatized protein. Protamine sulfate is the preferred salt form of protamine for use in the present invention.

To further extend the time action of the compositions of the present invention or to improve their suspendability, additional protamine and zinc may be added after crystallization. Thus, also within the present invention are formulations having protamine at higher than isophane ratios. For these formulations, the protamine ratio is from 0.25 mg to about 0.5 mg of protamine per mg of derivatized protein.

A required component of the microcrystals and precipitates of the present invention is a hexamer stabilizing compound. The structures of three hexameric conformations have been characterized in the literature, and are designated T6, T3R3, and R6. In the presence of hexamer stabilizing compound, such as various phenolic compounds, the R6 conformation is stabilized. Therefore, it is highly likely that hexamers are in the R6 conformation, or the T3R3 conformation in the crystals and precipitates produced in the presence of a hexamer stabilizing compound, such as phenol. A wide range of hexamer stabilizing compounds are suitable. At least 2 moles of hexamer stabilizing compound per hexamer of derivatized protein are required for effective hexamer stabilization. It is preferred that at least 3 moles of hexamer stabilizing compound per hexamer of derivatized protein be present in the microcrystals and precipitates of the present invention. The presence of higher ratios of hexamer stabilizing compound, at least up to 25 to 50-fold higher, in the solution from which the microcrystals and precipitates are prepared will not adversely affect hexamer stabilization.

In formulations of the present invention, a preservative may be present, especially if the formulation is intended to be sampled from multiple times. As mentioned above, a wide range of suitable preservatives are known. Preferably, the preservative is present in the solution in an amount suitable to provide an antimicrobial effect sufficient to meet pharmacopoeial requirements.

Preferred preservatives are the phenolic preservatives, which are enumerated above. Preferred concentrations for the phenolic preservative are from about 2 mg to about 5 mg per milliliter of the aqueous suspension formulation. These concentrations refer to the total mass of phenolic preservatives because mixtures of individual phenolic preservatives are contemplated. Suitable phenolic preservatives include, for example, phenol, m-cresol, and methylparaben. Preferred phenolic compounds are phenol and m-cresol. Mixtures of phenolic compounds, such as phenol and m-cresol, are also contemplated and highly preferred. Examples of mixtures of phenolic compounds are 0.6 mg/mL phenol and 1.6 mg/mL m-cresol, and 0.7 mg/mL phenol and 1.8 mg/mL m-cresol.

The microcrystals of the present invention are preferably oblong-shaped, single crystals composed of derivatized protein complexed with a divalent cation, and including a complexing compound and a hexamer-stabilizing compound. The mean length of the microcrystals of the present invention preferably is within the range of 1 micron to 40 microns, and more preferably is within the size range of 3 microns to 15 microns.

A preferred composition comprises from about 3 mg to about 6 mg of protamine sulfate per 35 mg of derivatized protein, and from about 0.1 to about 0.4 mg zinc per 35 mg of derivatized protein. Another preferred composition comprises from about 10 mg to about 17 mg of protamine sulfate per 35 mg of derivatized protein, and from about 2.0 to about 2.5 mg zinc per 35 mg of derivatized protein. Another preferred composition comprises, per mL, protamine sulfate, 0.34–0.38 mg; zinc, 0.01–0.04 mg; and derivatized protein, 3.2–3.8 mg.

The use of the present insoluble compositions to prepare a medicament for the treatment of diabetes or hyperglycemia is also contemplated. The amorphous precipitates and crystals of the present invention can be prepared for use in medicaments, or other used, by many different processes. In summary, suitable processes will generally follow the sequence: solubilization, hexamerization, complexation, precipitation, crystallization, and optionally formulation. Solubilization means the dissolution of derivatized protein sufficiently to allow it to form hexamers. Hexamerization refers to the process wherein molecules of derivatized protein bind with zinc(II) atoms to form hexamers. Complexation denotes the formation of insoluble complexes between the hexamers and protamine. Precipitation results typically from the formation of insoluble complexes. Crystallization involves the conversion of precipitated hexamer/protamine complexes into crystals, typically, rod-like crystals.

Solubilization is carried out by dissolving the derivatized protein in an aqueous solvent. The aqueous solvent may be, for example, an acidic solution, a neutral solution, or a basic solution. The aqueous solvent may be comprised partially of a miscible organic solvent, such as ethanol, acetonitrile, dimethylsulfoxide, and the like. Acidic solutions may be, for example, solutions of HCl, advantageously from about 0.01 N HCl to about 1.0 N HCl. Other acids that are pharmaceutically acceptable may be employed as well. Basic solutions may be, for example, solutions of NaOH, advantageously from about 0.01 N NaOH to about 1.0 N NaOH, or higher. Other bases that are pharmaceutically acceptable may be employed as well. For the sake of protein stability, the concentration of acid or base is preferably as low as possible while still being effective to adequately dissolve the derivatized protein.

Many derivatized proteins may be dissolved at neutral pH. Solutions to dissolve derivatized proteins at neutral pH may contain a buffer and optionally, salts, a phenolic compound or compounds, zinc, or an isotonicity agent.

The solution conditions required for hexamerization are those that allow the formation of derivatized protein-zinc hexamers in solution. Typically, hexamerization requires zinc and neutral pH. The presence of a hexamer-stabilizing compound advantageously influences the conformation of the derivatized protein in the hexamer, and promotes the R6 or the T3R3 hexamer conformations.

The complexation step must involve the combination of protamine with hexamer under solution conditions where each is initially soluble. This could be accomplished by combining separate solutions of hexameric derivatized protein and of protamine, or by forming a solution of derivatized protein and protamine at acidic or basic pH, and then shifting the pH to the neutral range.

During crystallization, the solution conditions must stabilize the crystallizing species. Thus, the solution conditions will determine the rate and outcome of the crystallization. Crystallization likely occurs through an equilibrium involving non-crystalline precipitated derivatized-protamine complexes, dissolved derivatized protein-protamine complex, and crystallized derivatized protein-protamine. The conditions chosen for crystallization drive the equilibrium toward crystal formation. Also, in light of the hypothesized equilibrium, the solubility of the derivatized protein is expected to profoundly affect rate and size because a lower solubility will slow the net conversion from precipitate to solution to crystal. Furthermore, it is well-recognized that slowing the rate of crystallization often results in larger crystals. Thus, the crystallization rate and crystal size are thought to depend on the size and nature of the derivatizing moiety on the derivatized protein.

Crystallization parameters that influence the crystallization rate and the size of crystals of the present invention are: acyl group size and nature; temperature; the presence and concentration of compounds that compete with derivatized protein for zinc, such as citrate, phosphate, and the like; the nature and concentration of phenolic compound(s); zinc concentration; the presence and concentration of a miscible organic solvent; the time permitted for crystallization; the pH and ionic strength; buffer identity and concentration; the concentration of precipitants; the presence of seeding materials; the shape and material of the container; the stirring rate; and the total protein concentration. Temperature and the concentration of competing compounds are thought to be of particular importance.

Competing compounds, such as citrate, affect the rate at which crystals form, and indirectly, crystal size and quality. These compounds may exert their effect by forming coordination complexes with zinc in solution, thus competing with the relatively weak zinc binding sites on the surface of derivatized protein hexamer for zinc. Occupation of these weak surface binding sites probably impedes crystallization. Additionally, many derivatized proteins are partially insoluble in the presence of little more than 0.333 zinc per mole of derivatized protein, and the presence of competing compounds restores solubility, and permits crystallization. The exact concentration of competing compound will need to be optimized for each derivatized protein. As an upper limit, of course, is the concentration at which zinc is precipitated by the competing compound, or the concentration at which residual competing compound would be pharmaceutically unacceptable, such as, when it would cause pain or irritation at the site of administration.

An example of a process for preparing the precipitates and crystals of the present invention follows. A measured amount of a powder of the derivatized protein is dissolved in an aqueous solvent containing a phenolic preservative. To this solution is added a solution of zinc as one of its soluble salts, for example $Zn(II)Cl_2$, to provide from about 0.3 moles of zinc per mole of derivatized insulin to about 0.7 moles, or to as much as 1.0 moles, of zinc per mole of derivatized insulin. Absolute ethanol, or another miscible organic solvent, may optionally be added to this solution in an amount to make the solution from about 5% to about 10% by volume organic solvent. This solution may then be filtered through a 0.22 micron, low-protein binding filter. A second solution is prepared by dissolving a measured amount of protamine in water equal to one tenth the concentration by weight of the aforementioned derivatized insulin solution. This solution is filtered through a 0.22 micron, low-protein binding filter. The derivatized insulin solution and the protamine solutions are combined in equal volumes, and the resulting solution is then stirred slowly at room temperature (typically about 20–25° C.) whereupon the microcrystals of the derivatized protein are formed within a period from about 12 hours to about 10 days.

The microcrystals may then be separated from the mother liquor and introduced into a different solvent, for storage and administration to a patient. Examples of appropriate aqueous solvents are as follows: water for injection containing 25 mM TRIS, 5 mg/mL phenol and 16 mg/mL glycerol; water for injection containing 2 mg/mL sodium phosphate dibasic, 1.6 mg/mL m-cresol, 0.65 mg/mL phenol, and 16 mg/mL glycerol; and water for injection containing 25 mM TRIS, 5 mg/mL phenol, 0.1 M trisodium citrate, and 16 mg/mL glycerol.

In a preferred embodiment, the crystals are prepared in a manner that obviates the need to separate the crystals from the mother liquor. Thus, it is preferred that the mother liquor itself be suitable for administration to the patient, or that the mother liquor can be made suitable for administration by dilution with a suitable diluent. The term diluent will be understood to mean a solution comprised of an aqueous solvent in which is dissolved various pharmaceutically acceptable excipients, including without limitation, a buffer, an isotonicity agent, zinc, a preservative, protamine, and the like.

In addition to the derivatized insulin, divalent cation, complexing compound, and hexamer-stabilizing compound, pharmaceutical compositions adapted for parenteral administration in accordance with the present invention may employ additional excipients and carriers such as water miscible organic solvents such as glycerol, sesame oil, aqueous propylene glycol and the like. When present, such agents are usually used in an amount ranging from about 0.5% to about 2.0% by weight based upon the final formulation. Examples of such pharmaceutical compositions include sterile, isotonic, aqueous saline solutions of the derivatized insulin derivative buffered with a pharmaceutically acceptable buffer and pyrogen free. For further information on the variety of techniques using conventional excipients or carriers for parenteral products, please see Remington's Pharmaceutical Sciences, 17th Edition, Mack Publishing Company, Easton, Pa., U.S.A. (1985), which is incorporated herein by reference.

In the broad practice of the present invention, it is also contemplated that a formulation may contain a mixture of the microcrystalline formulation and a soluble fraction of the derivatized insulin or a soluble fraction of normal insulin or rapid-acting insulin analog, such as, LysB28,ProB29-human insulin. Such mixtures are designed to provide a combination of meal-time control of glucose levels, which is provided by the soluble insulin, and basal control of glucose levels, which is provided by the insoluble insulin.

The following preparations and examples illustrate and explain the invention. The scope of the invention is not limited to these preparations and examples. Reference to "parts" for solids means parts by weight. Reference to "parts" for liquids means parts by volume. Percentages, when used to express concentration, mean mass per volume (×100). All temperatures are degrees Centigrade (° C.). "TRIS" refers to 2-amino-2-hydroxymethyl-1,3,-propanediol. The 1000 part-per-million (ppm) zinc solution was prepared by diluting 1.00 mL of a 10,000 ppm zinc atomic absorption standard solution [Ricca Chemical Company, zinc in dilute nitric acid] with water to a final volume of 10.00 mL.

In many of the preparations described below, the yield of precipitates and crystals was estimated. The yield estimate relied on determination of the amount of derivatized insulin or derivatized insulin analog in the precipitate or crystal, and on an estimate of the amount of the same initially in solution. To determine the amount of derivatized protein, samples of re-dissolved precipitate or crystal, and of the supernatant above the precipitate or crystals, were analyzed by reversed-phase gradient HPLC, as described below.

Briefly, the analytical system relied on a C8 reversed-phase column, at 23° C. The flow rate was 1.0 mL/min and UV detection at 214 nm was used. Solvent A was 0.1% (vol:vol) trifluroacetic acid in 10:90 (vol:vol) acetonitrile-:water. Solvent B was 0.1% (vol:vol) trifluroacetic acid in 90:10 (vol:vol) acetonitrile:water. The development program was (minutes, % B): (0.1,0); (45.1,75); (50.1,100); (55,100); (57,0); (72,0). All changes were linear. Other analytical systems could be devised by the skilled person to achieve the same objective.

To prepare for the HPLC analysis, aliquots of the well-mixed suspensions were dissolved by diluting with either 0.01 N HCl or 0.03 N HCl. HPLC analysis of these solutions gave the total mg/mL of derivatized protein. Aliquots of the suspensions were centrifuged for approximately 5 minutes in an Eppendorf 5415C microcentrifuge at 14,000 rpm. The decanted supernatant was diluted with either 0.01 N or 0.1 N HCl and analyzed by HPLC. The precipitate was washed by re-suspending in Dulbecco's phosphate buffered saline (without calcium or magnesium) and re-pelleted by centrifugation. The buffer was decanted and the solid was re-dissolved in 0.01 N HCl. The re-dissolved precipitate was analyzed by HPLC.

HPLC was used to confirm the presence of the expected proteins in the acidified suspension, re-dissolved precipitate, and supernatant and also to determine protein concentrations. The retention times of peaks in the chromatograms of the re-dissolved precipitates were compared with the retention times observed for protamine and the insulin compounds used to make the formulations. The agreement between retention times was always good, showing that the protamine and the derivatized proteins used to make the formulations were actually incorporated in the crystals. Concentrations of derivatized proteins were determined by comparing the appropriate peak areas to the areas of a standard. Protamine concentrations were not quantitated. A 0.22 mg/mL solution of derivatized insulin was used as the standard. A standard containing protamine was run, but only for the purpose of determining the retention time. Protamine concentration was not quantitated.

In many of the preparations described below, a standard spectrophotometric assay was used to determine how rapidly the crystals dissolved in Dulbecco's phosphate buffered saline (pH 7.4) at room temperature. Significant deviations from the procedure described immediately below are noted where appropriate in the descriptions of the preparations. A spectrophotometer suitable for measuring in the ultraviolet range, and equipped with a 1 cm cuvette and a magnetic cuvette stirrer was used for all the dissolution assays. The cuvette, containing a small stir bar and 3.00 mL of phosphate buffered saline (PBS), was put into the cell compartment of the spectrophotometer. The instrument was set to 320 nm and zeroed against the same buffer. Then 4.0 microliters of a well suspended formulation, usually having a total concentration approximately equivalent to a U50 formulation, or about 1.6 to 1.8 mg/mL, was added to the cuvette. After waiting 1.0 minute for mixing, the optical density at 320 nm was recorded. Since the proteins involved in this work do not absorb light at 320 nm, the decrease in optical density was due to reduction in light scattering as the crystals dissolved. The time for the optical density to drop to half of its initial value is typically reported (t½). As a control, 2.0 microliters of U100 Humulin® N (i.e., human insulin NPH, which is also known as human NPH insulin) was added to 3.00 mL of PBS buffer, and the optical density at 320 nm monitored as above. The dissolution half-time (t½) for the Humulin® N formulation was about 6 minutes.

Preparation 1

Gly(A21), Arg(B31), Arg(B32)-Human Insulin Analog

Gly(A21)Arg(B31)Arg(B32)-human insulin was obtained from an *E. coli* fermentation in which a Gly(A21)-human proinsulin precursor molecule was overexpressed into inclusion bodies. A portion (94.7 g) of inclusion bodies was solubilized in 500 mL of 6 M guanidine hydrochloride containing 0.1 M TRIS, 0.27 M sodium sulfite, and 0.1 M sodium tetrathionate, pH 10.5 at room temperature. The pH was quickly lowered to 8.8 with 12 N HCl. After vigorously stirring in an open container for 45 minutes the pH was lowered to 2.1 with phosphoric acid and the sample centrifuged overnight at 4° C. The supernatant was decanted and stored at 4° C. for additional processing. The pellet was re-extracted with 200 mL of additional pH 10.5 solution (see above) and then centrifuged for 3 hours at 4° C. This and the previously obtained supernatant were each diluted 4× with 100 mM sodium phosphate, pH 4, precipitating the product and other acidic components. After allowing the precipitate to settle, most of the supernatant was decanted and discarded. The resulting suspension was centrifuged, followed by decanting and discarding of additional supernatant, leaving wet pellets of the crude Gly(A21)-human proinsulin S-sulfonate precursor. The pellets were solubilized in 1.5 liters of 7 M deionized urea, adjusting the pH to 8 with 5 N NaOH and stirring over several hours at 4° C. Salt (NaCl) was then added to achieve 1 M concentration and the sample was loaded onto a XAD-7 column (14 cm×20 cm, Toso-Haas, Montgomeryville, Pa.), previously flushed with 50% acetonitrile/50% 50 mM ammonium bicarbonate, 10% acetonitrile/90% 50 mM ammonium bicarbonate, and finally with 7 M deionized urea/1M NaCl/20 mM TRIS, pH 8. Once loaded, the column was pumped with 4.5 liters of a 7 M deionized urea/1 M NaCl/20 mM TRIS, pH 8 solution, followed by 2.8 liters of 50 mM ammonium bicarbonate/1 M NaCl, and 6.5 liters of 50 mM ammonium bicarbonate. The column was eluted with a linear gradient of acetonitrile in 50 mM ammonium bicarbonate, while monitoring the eluant by UV at 280 nm. The peak of interest, partially purified Gly(A21)-human proinsulin S-sulfonate precursor, was collected, lyophilized, and subjected to a folding/disulfide bond procedure as follows. A quantity (5.4 g) of the precursor was dissolved in 3 liters of 20 mM glycine, pH 10.5, 4° C. Then, 15 mL of 240 mM cysteine HCl were added with stirring, while maintaining the pH at 10.5 and the temperature at 4° C. The reaction solution was stirred gently at 4° C. for 27 hours and then quenched by lowering the pH to 3.1 with phosphoric acid. Acetonitrile (155 mL) was added, and the solution was then loaded onto a 5×25 cm C4 reversed-phase column previously pumped with 60% acetonitrile/40% water/0.1% TFA and equilibrated in 10% acetonitrile/90% water/0.1% TFA. Once loaded the column was pumped with 1 liter of 17.5W acetonitrile/82.5% water/0.1% TFA, then eluted with a linear gradient of acetonitrile in 0.1% TFA while monitoring at 280 nm. Selected fractions were pooled and lyophilized with a recovery of 714 mg. For conversion of the proinsulin precursor to the desired insulin analog, 697 mg of the Gly(A21) human proinsulin precursor were dissolved in 70 mL 50 mM ammonium bicarbonate, then chilled to 4° C., pH 8.3. A volume (0.14 mL) of a 1 mg/mL solution of pork trypsin (Sigma Chemical Company, St. Louis, Mo.) in 0.01 N HCl was added to the sample solution which was stirred gently at 4° C. for about 24 hours. An additional 0.14 mL of the trypsin solution was added to the reaction solution which was then stirred for an additional 21 hours, 45 minutes. The reaction was quenched by lowering the pH to 3.2 with 0.7 mL glacial acetic acid and 0.3 mL phosphoric acid. The quenched Gly(A21)Arg(B31)Arg (B32)-human insulin sample solution from the tryptic cleavage reaction was diluted 4× with 30% acetonitrile/70% 50 mM acetic acid, pH 3.1, and loaded onto a 1×30 cm S HyperD F (Biosepra, Marlborough, Mass.) cation exchange column previously pumped with 30% acetonitrile/70% 50 mM acetic acid/500 mM NaCl, pH 3.3, and equilibrated in 30% acetonitrile/70% 50 mM acetic acid. Once loaded the column was pumped with about 50 mL of 30% acetonitrile/70% 50 mM acetic acid, then eluted with a linear gradient of NaCl in 30% acetonitrile/50 mM acetic acid while monitoring the eluant at 276 nm. Selected fractions containing the Gly(A21)Arg(B31)Arg(B32)-human insulin were pooled, diluted 3× with purified water and loaded onto a 2.2×25 cm C4 reversed-phase column (Vydac, Hesperia, Calif.) previously pumped with 60% acetonitrile/40% water/0.1% TFA, then 10% acetonitrile/90% water/0.1% TFA. Once loaded, the column was pumped with about 200 mL of 10% acetonitrile/90% water/0.1% TFA, then eluted with a linear gradient of acetonitrile in 0.1% TFA. Selected fractions were pooled and lyophilized giving a recovery of 101 mg. Analytical HPLC revealed a purity of greater that 95% main peak. Electrospray mass spectroscopy (ESMS) analysis of the purified protein yielded a molecular weight of 6062.9 (6063.0, theory).

Preparation 2

Des(B30)-Human Insulin

Des(B30)-human insulin was prepared from human proinsulin by controlled tryptic hydrolysis. A mass (2 g) of human proinsulin biosynthesized in recombinant *E. coli* and purified by conventional methods [Frank, B. H., et al., in *PEPTIDES: Synthesis-Structure-Function. Proceedings of the Seventh American Peptide Symposium,* Rich, D. H. and Gross, E. (Eds.), Pierce Chemical Company, Rockford, pp. 729–738, 1981; also, Frank, B. H., U.S. Pat. No. 4,430,266, issued Feb. 7, 1984, each of which is incorporated by reference] were dissolved in 400 mL of 0.1 M, pH 7.5 HEPES buffer. After addition of 8 mL of 1 M $CaCl_2$ (in water) and pH adjustment to 7.5 with 5 N NaOH, 2 mL of a 10 mg/mL solution of pork trypsin (Sigma) in 0.01 N HCl were transferred to the sample solution while gently stirring. The reaction solution was allowed to stir at ambient temperature for 2 hours and 42 minutes, at which time it was transferred to a 37° C. environment while stirring occasionally. After 1 hour and 45 minutes at 37° C. the enzymatic reaction was quenched by lowering the pH to 3.0 with phosphoric acid and the temperature to 4° C. for storage. Subsequently, the solution was brought to room temperature and diluted with 50 mL acetonitrile, then to a final volume of 500 mL with purified water, then loaded onto a 2.5×58 cm CG-161 (Toso-Haas) column previously pumped with 1 c.v. (column volume) of 40% acetonitrile/60% 0.1 M ammonium sulfate, pH 2.5, and 2 c.v. of 10% acetonitrile/90% 0.1 M ammonium sulfate, pH 2.5. Once loaded the column was pumped with 1 c.v. of 10% acetonitrile/90% 0.1 M ammonium sulfate, pH 2.5. The column was eluted with a linear gradient of acetonitrile in 0.1 M ammonium sulfate, pH 2.5, while monitoring the eluant at 276 nm. The peak of interest, partially purified des(B30)-human insulin, was collected by pooling selected fractions. This pooled sample of partially purified des(B30)-human insulin was diluted to 1.28 liters with purified water, pH 3.5, and applied to a 1×29 cm S HyperD F (Biosepra) cation exchange column previously pumped with 1 c.v. of 30% acetonitrile/70% 0.1% TFA/0.5 M NaCl, pH 1.9, and 2 c.v. of 30% acetonitrile/70% 0.1% TFA, pH 2.3. Once loaded the column was pumped with 1 c.v. 30% acetonitrile/70% 0.1% TFA, pH 2.3, then eluted with a linear gradient of NaCl in 30% acetonitrile/70% 0.1% TFA, pH 1.9 to 2.3, while monitoring the eluant at 276 nm. Selected fractions containing the purified des(B30)-human insulin were pooled, diluted 2.5× with purified water and loaded onto a 35-c.c. C8 SepPak (Waters, Milford, Mass.) previously cleaned and primed with 2 c.v. of acetonitrile, 2 c.v. of 60% acetonitrile/40% 0.1% TFA, and 2 c.v. of 10% acetonitrile/90% 0.1% TFA. Once loaded the SepPak was flushed with 3 c.v. of 10% acetonitrile/90% 0.1% TFA and then eluted with 2 c.v. of 60% acetonitrile/40% 0.1% TFA. The lyophilized eluant yielded 500 mg. An analytical HPLC assay suggested greater than 95% main peak. Electrospray mass spectroscopy (ESMS) analysis of the purified protein yielded a molecular weight of 5706.5 (5707, theory).

Preparation 3

Rabbit Insulin

Rabbit insulin was prepared as described in Chance, R. E., et al. [*Proinsulin, Insulin, C-Peptide,* Baba, S., et al. (Eds.), *Excerpta Medica,* Amsterdam-Oxford, pp. 99–105 (1979)].

Preparation 4

Asp(B28)-Human Insulin Analog

Asp(B28)-human insulin was prepared and purified essentially according to the teaching of examples 31 and 32 of Chance, R. E., et al. (U.S. Pat. No. 5,700,662, issued Dec. 23, 1997) which is expressly incorporated herein by reference. Des(B23–30)-human insulin [Bromer, W. W. and Chance, R. E., *Biochim. Biophys. Acta,* 133:219–223 (1967), which is incorporated herein by reference] and a synthetic octapeptide Gly-Phe-Phe-Tyr-Thr-Asp-Lys(Tfa)-Thr were condensed using trypsin-assisted semisynthesis, purified by gel filtration and reversed-phased HPLC, treated with 15% ammonium hydroxide (v/v) for four hours at ambient temperature to remove the trifluoroacetate (Tfa) blocking group from Lys(B29), purified by reversed-phase HPLC, and lyophilized.

Preparation 5

Syntheses of Derivatized Proteins

The following is an outline of the syntheses of certain derivatized proteins used to prepare the precipitates and crystals of the present invention. The outline is to be read together with the data in Table 2, below.

A measured mass of purified insulin or of an insulin analog was dissolved in a measured volume of dimethylsulfoxide (DMSO) with stirring. Then, a measured volume of tetramethylguanidine hydrochloride (TMG) was added and the solution mixed thoroughly. In a separate container, a measured mass of an N-acyl-succinimide (NAS) was dissolved in a measured volume of DMSO. A measured volume of the second solution was added to the first solution. The reaction was carried out at room temperature, and the progress of the reaction was monitored by analyzing samples of the reaction mixture using HPLC. The reaction was quenched by adding a measured volume of ethanolamine, and then acidifying to pH 2–3.

The reaction mixture was then subjected to purification using reversed-phase chromatography alone, or using a combination of cation exchange chromatography followed by reversed-phase chromatography. The reversed-phase purification was carried out using an FPLC® system (Pharmacia) with UV detection at 214 nm or at 280 nm, a fraction collector, 2.2×25 cm or 5×30 cm C18 column, 2.5 or 5 mL/min flow rate, at room temperature. The liquid phases were mixtures of Solution A [0.1% trifluroacetic acid (TFA) in 10:90 acetonitrile:water (vol:vol)] and Solution B [0.1% trifluoroacetic acid (TFA) in 70:30 acetonitrile:water (vol:vol)] appropriate to elute and separate the species of interest. Typically, the column was equilibrated and loaded while in 100% Solution A. Then, a linear gradient to some proportion of Solution B was used to separate the reaction products adequately. Fractions containing product were pooled. The development of purification methods is within the skill of the art.

Table 2 below provides experimental data, according to the outline above, for the synthesis of the derivatized proteins that were used to prepare various embodiments of the present invention. The starting proteins were prepared as described above, or according to conventional methods. Conventional purification was used to provide highly purified starting proteins for the syntheses described below. The synthesis of insulin, insulin analogs, and proinsulin is within the skill of the art, and may be accomplished using recombinant expression, semisythesis, or solid phase synthesis followed by chain combination. The purification of synthesized proteins to a purity adequate to prepare the derivatives used in the present invention is carried out by conventional purification techniques.

Molecular weight of the purified derivatives was confirmed by mass spectrometry via electrospray mass analysis (ESMS). Assignment of the acylation site was based either on a chromatographic analysis ("HPLC"), or on an N-terminal analysis ("N-terminal"), or both.

TABLE 2

Summary of synthesis of various derivatized proteins.

| Starting protein | human insulin | human insulin | human insulin |
|---|---|---|---|
| protein mass (mg) | 141.3 | 1,080 | 120 |
| DMSO (mL) | 42 | 30 | 36 |
| TMG (µL) | 30.5 | 233 | 25.9 |
| NAS acyl chain | n-hexanoyl | n-octanoyl | n-dodecanoyl |
| Mass of NAS (mg) | 7.76 | 85.7 | 9.22 |
| Volume of DMSO (mL) | 1.0 | 1.0 | 0.701 |
| Volume of NAS solution added (mL) | 0.494 | 0.785 | 0.701 |
| Reaction time (min) | 40 | 105 | 40 |
| Ethanolamine volume (µL) | 20 | 100 | 120 |
| Total yield (%) | 40 | 33 | 36 |
| Mol. Wt. (theory) | 5906.0 | 5933.9 | 5990.0 |
| Mol. Wt. (ESMS) | 5906.8 | 5933.9 | 5990.0 |
| HPLC Purity (%) | 96 | 94 | 98 |
| Acylation site (HPLC) | Nε | Nε | Nε |
| Acylation site (N-terminal) | Nε | Nε | Nε |
| protein mass (mg) | 194 | 2040 | 2050 |
| DMSO (mL) | 60 | 62 | 58 |
| TMG (µL) | 41.9 | 441 | 443 |
| NAS acyl chain | n-tetradecanoyl | n-butyryl | n-hexanoyl |
| Mass of NAS (mg) | 23.4 | 269.3 | 209 |
| Volume of DMSO (mL) | 1.0 | 1.0 | 2.0 |
| Volume of NAS solution added (mL) | 0.756 | 0.29 | 1.44 |
| Reaction time (min) | 20 | 30 | 30 |
| Ethanolamine volume (µL) | 5 | 100 | 100 |
| Total yield (%) | 45 | 27* | 22 |
| Mol. Wt. (theory) | 6018.1 | 5877.8 | 5905.9 |
| Mol. Wt. (ESMS) | 6018.2 | 5877.8 | 5906.0 |
| HPLC Purity (%) | 98 | 94 | 93 |
| Acylation site (HPLC) | Nε | Nε | Nε |
| Acylation site (N-terminal) | Nε | — | — |

*purification involved first reversed-phase HPLC, then cation exchange HPLC, then reversed-phase HPLC The following is an outline of the synthesis of additional derivatized proteins. The outline is to be read together with the data in Table 3, below, to provide full synthetic schemes.

A measured mass of purified insulin or of an insulin analog was dissolved by adding to it a measured volume of 50 mM boric acid, pH 2.57. A measured volume of acetonitrile, equal to the volume of boric acid solution, was then added slowly with stirring. The "solvent" volume is the sum of the volumes of the boric acid and acetonitrile. The pH of the solution was adjusted to between 10.2 and 10.5 using NaOH. In a separate container, a measured mass of an N-acyl-succinimide ("NAS") was dissolved in a measured volume of DMSO. A measured volume of the second solution was added to the first solution. The reaction was carried out at room temperature, the pH was maintained above 10.2 as necessary, and the progress of the reaction was monitored by analyzing samples of the reaction mixture using HPLC. The reaction was quenched by acidifying to pH 2–3. The reaction mixture was then subjected to purification using a reversed-phase chromatography system as described above.

Table 3 provides experimental data, according to the outline above, for the synthesis of the derivatized proteins that were used to prepare various embodiments of the present invention. Molecular weight of the purified derivatives was confirmed by mass spectrometry via electrospray mass analysis (ESMS). Assignment of the acylation site was based either on a chromatographic analysis ("HPLC"), or on an N-terminal analysis ("N-terminal"), or both.

TABLE 3

Summary of synthesis of various derivatized proteins.

| Starting protein | human insulin | human insulin | human insulin |
|---|---|---|---|
| protein mass (mg) | 2,170 | 2,420 | 2,250 |
| solvent (mL) | 200 | 240 | 200 |
| NAS acyl chain | n-butyryl | n-pentanoyl | n-octanoyl |
| Mass of N-acyl-succinimide (mg) | 108.7 | 1155 | 173 |
| Volume of DMSO (mL) | 1.0 | 5 | 1.0 |
| Volume of NAS solution added (mL) | 0.955 | 0.719 | 0.81 |
| Reaction time (min) | 40 | 40 | 40 |
| Total yield (%) | 25 | 12 | 37 |
| Mol. Wt. (theory) | 5877.8 | 5891.8 | 5933.9 |
| Mol. Wt. (ESMS) | 5877.7 | 5891.9 | 5933.8 |
| HPLC Purity (%) | 96 | 95 | 96 |
| Acylation site (HPLC) | Nε | Nε | Nε |

| Starting protein | human insulin | human insulin | human insulin |
|---|---|---|---|
| protein mass (mg) | 1,960 | 2,750 | 1,040 |
| solvent (mL) | 200 | 200 | 200 |
| NAS acyl chain | n-nonanoyl | n-dodecanoyl | n-tetradecanoyl |
| Mass of N-acyl-succinimide (mg) | 145.8 | 19.9 | 102.3 |
| Volume of DMSO (mL) | 1.0 | 1.0 | 1.0 |
| Volume of NAS solution added (mL) | 0.887 | 0.771 | 0.885 |
| Reaction time (min) | 40 | 30 | 35 |
| Total yield (%) | 35 | 14 | 39 |
| Mol. Wt. (theory) | 5947.9 | 5990.0 | 6018.1 |
| Mol. Wt. (ESMS) | 5948.1 | 5989.9 | 6018.1 |
| HPLC Purity (%) | 94 | 93 | 94 |
| Acylation site (HPLC) | Nε | Nε | Nε |

| Starting protein | sheep insulin | beef insulin | pork insulin |
|---|---|---|---|
| protein mass | 312 | 275 | 200 |
| solvent (mL) | 100 | 100 | 100 |
| NAS acyl chain | n-hexanoyl | n-hexanoyl | n-octanoyl |
| Mass of N-acyl-succinimide (mg) | 27.2 | 19.9 | 16.4 |
| Volume of DMSO (mL) | 1.0 | 1.0 | 1.0 |
| Volume of NAS solution added (mL) | 0.644 | 0.771 | 0.764 |
| Reaction time (min) | 45 | 30 | 82 |
| Total yield (%) | 31 | 50 | 41 |
| Mol. Wt. (theory) | 5801.7 | 5831.8 | 5903.9 |
| Mol. Wt. (ms) | 5801.8 | 5831.7 | 5903.9 |
| HPLC Purity (%) | 96 | 96 | 96 |
| Acylation site (HPLC) | Nε | Nε | Nε |

| Starting protein | rabbit insulin | des(B30)-human insulin | AspB28-human insulin |
|---|---|---|---|
| Protein mass (mg) | 211.4 | 205.3 | 132.3 |
| Solvent (mL) | 100 | 20 | 20 |
| NAS acyl chain | n-octanoyl | n-octanoyl | n-octanoyl |
| Mass of N-acyl-succinimide (mg) | 16.8 | 21.5 | 11.5 |
| Volume of DMSO (mL) | 1.0 | 0.5 | 1.0 |
| Volume of NAS | 0.786 | 0.303 | 0.715 |

TABLE 3-continued

Summary of synthesis of various derivatized proteins.

| solution added (mL) | | | |
|---|---|---|---|
| Reaction time (min) | 57 | 40 | 85 |
| Total yield (%) | 39 | 47 | 32 |
| Mol. Wt. (theory) | 5919.9 | 5833.6 | 5951.9 |
| Mol. Wt. (ms) | 5920.0 | 5832.7 | 5952.2 |
| HPLC Purity (%) | 95 | 96 | 94 |
| Acylation site (HPLC) | Nε | Nε | Nε |

| Starting protein | GlyA21, ArgB31, ArgB32-human insulin analog | human insulin | des(B27)-human insulin analog |
|---|---|---|---|
| Protein mass (mg) | 86.2 | 134.8 | 44.8 |
| Solvent (mL) | 10 | 20 | 7 |
| NAS acyl chain | n-octanoyl | 2-methyl-hexanoyl | n-octanoyl |
| Mass of N-acyl-succinimide (mg) | 22.4 | 749 | 3.6 |
| Volume of DMSO (mL) | 0.5 | 4.93* | 1.0 |
| Volume of NAS solution added (mL) | 0.115 | 0.052 | 0.993 |
| Reaction time (min) | 40 | 45 | 40 |
| Total yield (%) | 45 | 45 | 53 |
| Mol. Wt. (theory) | 6189.2 | 5919.9 | 5832.8 |
| Mol. Wt. (ms) | 6189.2 | 5919.9 | 5832.9 |
| HPLC Purity (%) | 97 | 96 | 93 |
| Acylation site (HPLC) | Nε | Nε | Nε |

| Starting protein | human insulin | human insulin | human insulin |
|---|---|---|---|
| Protein mass (mg) | 160 | 147.7 | 2,080 |
| Solvent (mL) | 20 | 20 | 200 |
| NAS acyl chain | 4-methyl-octanoyl | 3-methyl-decanoyl | n-octanoyl |
| Mass of N-acyl-succinimide (mg) | 715 | 22.5 | 146.7 |
| Volume of DMSO (mL) | 4.97* | 1.0* | 1.0* |
| Volume of NAS solution added (mL) | 0.0734 | 0.609 | 0.884 |
| Reaction time (min) | 60 | 45 | 40 |
| Total yield (%) | 54 | 38 | 5.3** |
| Mol. Wt. (theory) | 5947.9 | 5976.0 | 6060.1 |
| Mol. Wt. (ms)*** | 5947.8 | 5976.2 | 6060.5 |
| HPLC Purity (%) | 96 | 96 | 92 |
| Acylation site (HPLC) | Nε | Nε | A1-Nα, Nε |

| Starting protein | des(B30)-human insulin analog | human insulin | human insulin |
|---|---|---|---|
| Protein mass (mg) | 205.3 | 1,960 | 2,110 |
| Solvent (mL) | 20 | 200 | 200 |
| NAS acyl chain | n-octanoyl | n-nonanoyl | n-decanoyl |
| Mass of N-acyl-succinimide (mg) | 21.5 | 145.8 | 150.5 |
| Volume of DMSO (mL) | 1.0 | 1.0 | 1.0 |
| Volume of NAS solution added (mL) | 0.089 | 0.0887 | 0.975 |
| Reaction time (min) | 40 | 40 | 60 |
| Total yield (%) | 11.0 | 11.5 | 11.1 |
| Mol. Wt. (theory) | 5959.5 | 6088.2 | 6116.2 |
| Mol. Wt. (ms) | 5959.3 | 6088.3 | 6116.4 |
| HPLC Purity (%) | 96 | 92 | 92 |
| Acylation site (HPLC) | A1-Nα, Nε | A1-Nα, Nε | A1-Nα, Nε |

*Dissolved in acetonitrile instead of DMSO.
**Yield of the A1-Nα,B29-Nε-diacyl-human insulin derivative
***Determined by Matrix-Assisted Laser Desorption Ionization (MALDI) mass spectroscopy instead of electrospray mass spectroscopy Preparation 6

Microcrystals of B29-Nε-octanoyl-LysB29 Human Insulin

A dry powder of B29-Nε-octanoyl-LysB29 human insulin (7 parts by mass) is dissolved in 1000 parts by volume of an aqueous solvent composed of 25 mM TRIS, 0.1 M trisodium citrate, and 10 mg/mL phenol at pH 7.6. To this solution is added 150 parts of a 15.3 mM solution of zinc chloride. The pH is adjusted to 7.6 with 1 N HCl and/or 1 N NaOH. Then 120 parts by volume of ethanol are added. This solution is filtered through a 0.22 micron, low-protein binding filter. A second solution is prepared by dissolving 6 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. This suspension is stirred slowly for 24 hours at room temperature (typically about 22° C. ). The amorphous precipitate converts to a microcrystalline solid.

Preparation 7

Formulation of Microcrystals of B29-Nε-octanoyl-LysB29 Human Insulin

The microcrystals prepared by the method of Preparation 6 are separated from the mother liquor and are recovered by conventional solid/liquid separation methods, such as, filtration, centrifugation, or decantation. The recovered microcrystals are then suspended in a solution consisting of 25 mM TRIS, 5 mg/mL phenol, and 16 mg/mL glycerol, pH 7.4, so that the final concentration of acylated insulin corresponds to the equivalent of a 100 U/mL solution of insulin.

Preparation 8

Microcrystals of B29-Nε-hexanoyl-LysB29 Human Insulin

A dry powder of B29-Nε-hexanoyl-LysB29 human insulin (7 parts by mass) is dissolved in 1000 parts by volume of an aqueous solvent composed of 25 mM TRIS, 0.1 M trisodium citrate, 10 mg/mL phenol, and 16 mg/mL glycerol at pH 7.6. To this solution is added 150 parts of a 15.3 mM solution of zinc chloride. The pH is adjusted to 7.6 with 1 N HCl and/or 1 N NaOH. Then 120 parts by volume of ethanol are added. This solution is filtered through a 0.22 micron, low-protein binding filter. A second solution is prepared by dissolving 6 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. This suspension is stirred slowly for 24 hours at room temperature (typically about 22° C. ). The amorphous precipitate converts to a microcrystalline solid.

Preparation 9

Formulation of Microcrystals of B29-Nε-hexanoyl-LysB29 Human Insulin

The microcrystals prepared by the method of Preparation 8 are separated from the mother liquor and are recovered by conventional solid/liquid separation methods. The recovered microcrystals are then suspended in a solution consisting of 2 mg/mL sodium phosphate dibasic, 1.6 mg/mL m-cresol, 0.65 mg/mL phenol, and 16 mg/mL glycerol, pH 6.8, so that the final concentration of acylated insulin corresponds approximately to the concentration equivalent of a 100 U/mL solution of insulin.

Preparation 10

Microcrystals of B28-Nε-octanoyl-LysB28,ProB29-Human Insulin

A dry powder of B28-Nε-octanoyl-LysB28-LysB28, ProB29-human insulin (7 parts by mass) is dissolved in 1000 parts by volume of an aqueous solvent composed of 25 mM TRIS, 0.1 M trisodium citrate, and 10 mg/mL phenol at pH 7.6. To this solution is added 150 parts of a 15.3 mM solution of zinc chloride. The pH is adjusted to 7.6 with 1 N HCl and/or 1 N NaOH. Then 120 parts by volume of ethanol are added. This solution is filtered through a 0.22 micron, low-protein binding filter. A second solution is prepared by dissolving 6 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. After 24 hours at room temperature (typically about 22°C.), the amorphous precipitate converts to a microcrystalline solid.

Preparation 11

Formulation of Microcrystals of B28-Nε-octanoyl-LysB28,ProB29-Human Insulin

The microcrystals prepared by the method of Preparation 10 are separated from the mother liquor and are recovered by conventional solid/liquid separation methods. The recovered microcrystals are then suspended in a solution consisting of 25 mM TRIS, 5 mg/mL phenol, 0.1 M trisodium citrate, and 16 mg/mL glycerol, pH 7.6, so that the final concentration of acylated insulin corresponds approximately to the concentration equivalent of a 100 U/mL solution of insulin.

Preparation 12

Microcrystals of B28-Nε-butyryl-LysB28,ProB29-Human Insulin

A dry powder of B29-Nε-butyryl-LysB29 human insulin (7 parts by mass) is dissolved in 1000 parts by volume of an aqueous solvent composed of 25 mM TRIS, 0.1 M trisodium citrate, and 10 mg/mL phenol at pH 7.6. To this solution is added 150 parts of a 15.3 mM solution of zinc chloride. The pH is adjusted to 7.6 with 1 N HCl and/or 1 N NaOH. Then 120 parts by volume of ethanol are added. This solution is filtered through a 0.22 micron, low-protein binding filter. A second solution is prepared by dissolving 6 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. After 24 hours at room temperature (typically about 22° C.), the amorphous precipitate converts to a microcrystalline solid.

Preparation 13

Formulation of Microcrystals of B28-Nε-butyryl-LysB28,ProB29-Human Insulin

The microcrystals prepared by the method of Preparation 7 are separated from the mother liquor and are recovered by conventional solid/liquid separation methods. The recovered microcrystals are then suspended in a solution consisting of 25 mM TRIS, 2.5 mg/mL m-cresol, and 16 mg/mL glycerol, pH 7.8, so that the final concentration of acylated insulin corresponds approximately to the concentration equivalent of a 100 U/mL solution of insulin.

Preparation 14

Microcrystals of B29-Nε-butyryl-Human Insulin

B29-Nε-butyryl-human insulin was prepared as described in Preparation 5. A sample of B29-Nα-butyryl-human insulin (16.21 mg) was dissolved in 0.8 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of crystallization diluent was added, and the resulting mixture was stirred until completely mixed. The crystallization diluent was prepared by dissolving in water, with stirring, 0.603 g of TRIS, 1.007 g of phenol, 1.582 g of glycerol and 2.947 g of trisodium citrate. Further water was added to bring the of the solution to 100 mL. After mixing the zinc-insulin derivative solution with the crystallization diluent, the pH of the resulting solution was adjusted to 7.59 using small aliquots of 1 N HCl and 1 N NaOH, as needed. The pH-adjusted solution was filtered through a 0.22 micron, low-protein binding filter. To a volume of the filtered solution was added an equal volume of an aqueous solution of protamine, prepared by dissolving 18.59 mg of protamine sulfate in water to a final volume of 50 mL. The mixture of the two volumes was swirled gently to complete mixing, and then allowed to stand at 25° C. Rod-like crystals formed in very high yield (greater than 90%). In the spectrophotometric dissolution assay described above, the crystals of B29-Nε-butyryl-human insulin had a t½ of 32–33 minutes, compared with about 6 minutes for Humulin® N in the same assay.

Preparation 15

Microcrystals of B29-Nε-pentanoyl-Human Insulin

B29-Nε-pentanoyl-human insulin was prepared as described in Preparation 5. A sample of B29-Nε-pentanoyl-human insulin (16.14 mg) was dissolved in 0.8 mL of 0.1 N HCl. The procedure described in Preparation 14 was followed, except the pH was adjusted to 7.60, and the protamine solution contained 18.64 mg of protamine sulfate in a total volume of 50 mL. Rod-like crystals formed in high yield (greater than 80%). In the spectrophotometric dissolution assay described above, the crystals of B29-Nε-pentanoyl-human insulin had a t½ of 33–34 minutes, compared with about 6 minutes for Humulin® N in the same assay.

Preparation 16

Microcrystals of B29-Nε-hexanoyl-Human Insulin

B29-Nε-hexanoyl-human insulin was prepared as described in Preparation 5. A sample of B29-Nε-hexanoyl-human insulin (15.87 mg) was dissolved in 0.8 mL of 0.1 N HCl. The procedure described in Preparation 14 was followed, except the pH was adjusted to 7.58. Rod-like crystals formed in very high yield (greater than 90%). In the spectrophotometric dissolution assay described above, the crystals of B29-Nε-hexanoyl-human insulin had a t½ of 69–70 minutes, compared with about 6 minutes for Humulin® N in the same assay.

Preparation 17

Microcrystals of B29-Nε-(2-methylhexanoyl)-Human Insulin

B29-Nε-(2-methylhexanoyl)-human insulin was prepared as described in Preparation 5. A mass (8.19 mg) of B29-Nε-(2-methylhexanoyl)-human insulin was dissolved in 0.400 mL of 0.1 N HCl. After stirring for 5–10 minutes, 0.160 mL of a zinc nitrate solution containing 1000 parts-per-million (ppm) zinc(II) was added and the resulting solution was mixed thoroughly. Then, 1.60 mL of diluent (in 100 mL: 0.604 g TRIS, 1.003 g phenol, 3.218 g glycerol, and 3.069 g trisodium citrate) was added and mixed. The pH of this solution was adjusted to 7.61 with small quantities of 1.0 N HCl and 1.0 N NaOH, and then the solution was filtered through a 0.22 micron, low-protein binding filter. To 2 mL of this filtered solution was added 2 mL of a protamine solution (in 100 mL, 37.41 mg of protamine). The mixture was swirled gently. A precipitate formed. The mixture was left undisturbed at 25° C. Rod-like crystals formed in good yield (greater than 65%). In the spectrophotometric dissolution assay described above, the crystals of B29-Nε-2-methylhexanoyl-human insulin had a t½ of 23 minutes, compared with about 6 minutes for Humulin® N in the same assay.

Preparation 18

Microcrystals of B29-Nε-octanoyl-Human Insulin

B29-Nε-octanoyl-LysB29 human insulin (4.17 mg) was dissolved in 1 mL of a solvent composed of 25 mM TRIS, 0.1 M trisodium citrate, and 10 mg/mL phenol at pH 7.6. To this solution, 0.15 mL of a 15.3 mM solution of zinc chloride was added. The resulting solution was adjusted to a pH of 7.6 with 1 N NaOH. To this solution 0.12 mL of ethanol was added. The resulting solution was filtered through a 0.22 micron, low-protein binding filter. A second solution was prepared by dissolving 3.23 mg of protamine sulfate in 10 mL of water then filtered through a 0.22 micron, low-protein binding filter. A volume of 1 mL of the B29-Nε-octanoyl-LysB29 human insulin solution and 1 mL of the protamine sulfate solution were combined, resulting in the immediate appearance of an amorphous precipitate. This solution was divided into two 1 mL portions which were transferred to vials then gently agitated for 19 hours at room temperature (approximately 22° C.), using an automatic wrist-action shaker. This procedure resulted in the formation of a white-to-off-white microcrystalline solid. HPLC analysis of crystals that have been removed from the mother liquor and thoroughly washed demonstrated the presence of protamine within the crystalline material.

Preparation 19

Crystalline suspension formulation comprising Nε-octanoyl-Human Insulin

An acidic solution of Nε-octanoyl-human insulin was prepared by dissolving 39.7 mg of Nε-octanoyl-human insulin in 1 mL of 0.1 N HCl. This solution was stirred for approximately 5 minutes. To this solution was added 0.4 mL of a zinc nitrate solution containing 1000 parts-per-million (ppm) zinc(II) with stirring. The zinc nitrate solution was a 1:10 dilution of a 10,000 ppm Zn(II) atomic absorption standard. To the Nε-octanoyl-human insulin plus zinc solution was added 4 mL of a crystallization diluent (40 mg/mL glycerol, 50 mM TRIS, 4 mg/mL m-cresol, 1.625 mg/mL phenol, 100 mM trisodium citrate, pH 7.4). The pH of the resulting solution was adjusted to 7.61. The pH-adjusted solution was filtered through a 0.22 micron, low protein-binding filter. Five milliliters (5 mL) of protamine solution (37.6 mg of protamine sulfate in 50 mL of water) were added to 5 mL of the filtered Nε-octanoyl-human insulin solution. The solution was allowed to stand undisturbed for 63 hours at a controlled temperature of 25° C.

Microscopic inspection (at 63 hours) revealed that crystallization had occurred and that the preparation had yielded uniform, single, rod-like crystals possessing approximate average lengths of about 10 microns.

The crystals were sedimented by allowing the formulation to stand undisturbed. Eight milliliters (8 mL) of the supernatant were then removed, and were replaced with 8 mL of a diluent [16 mg/mL glycerol, 20 mM TRIS, 1.6 mg/mL m-cresol, 0.65 mg/mL phenol, 40 mM trisodium citrate, pH 7.4]. The crystals were then resuspended. This procedure was carried out in the same way three times, except that on the third occasion, the 8 mL of supernatant was replaced with 7 mL of diluent.

The amount of insulins in the formulation was analyzed by HPLC to quantitate the total potency. The total potency refers to the total concentration of human insulin and Nε-hexanoyl-human insulin. An aliquot (0.050 mL) of the fully resuspended formulation was dissolved in 0.950 mL of 0.01 N HCL, and subjected to HPLC analysis, as described below. For HPLC analyses, the following conditions were used: a C8-reversed-phase column; constant 23° C.; 1.0 mL/min, detection at 214 nm; solvent A=10% acetonitrile (vol/vol) in 0.1% aqueous trifluoroacetic acid; solvent B=90% acetonitrile (vol/vol) in 0.1% aqueous trifluoroacetic acid; linear gradients (0.1 min, 0% B; 45.1 min, 75% B; 50.1 min, 100% B; 55 min 100% B; 57 min, 0% B; 72 min, 0% B). Standards were prepared by dissolving bulk insulin and bulk acyl insulin in 0.01 N HCl. The concentration of each standard was determined by UV spectroscopy. A solution of 1.000 mg/mL of human insulin in a 1 cm cuvette was assumed to have an absorbance of 1.05 optical density units at the wavelength maximum (approximately 276 nm). This corresponds to a molar extinction coefficient of 6098. Acylated insulins were assumed to have the same molar extinction coefficient as human insulin. The solutions calibrated by UV were then diluted to get standards at 0.220, 0.147, 0.073, and 0.022 mg/mL. The standards were run on HPLC and a standard curve of area vs. concentration was obtained.

Total potency of Nε-octanoyl-human insulin in the crystal formulation was 3.76 mg/mL. The concentration of soluble Nε-octanoyl-human insulin was determined to be 0.01 mg/mL. No unacylated human insulin was found by HPLC analysis.

The dissolution rate of the crystals was measured by placing 0.005 mL of the uniformly suspended formulation into 3 mL of Dulbecco's phosphate buffered saline (without calcium or magnesium) in a 1 cm path length square quartz cuvette at a temperature of 22° C. This solution was stirred at a constant rate using a magnetic cuvette stirrer. Absorbance measurements at 320 nm were taken at 1 minute intervals. The absorbance at 320 nm corresponds to the light scattered by the insoluble particles present in the aqueous suspension. Consequently, as the microcrystals dissolve, the absorbance approaches zero. The approximate time required for the 0.005 mL of this formulation to dissolve was more than 400 minutes. The time required for a 0.005 mL sample of U100 commercial Humulin® N to dissolve under the same conditions was about 10 minutes.

Particle size measurement was performed on a sample of the formulation utilizing a particle sizing instrument (Multisizer Model IIE, Coulter Corp., Miami, Fla. 33116-9015). To perform this measurement, 0.25 mL of the crystal formulation was added to 100 mL of a diluent consisting 14 mM dibasic sodium phosphate, 16 mM glycerol, 1.6 mg/mL m-cresol, 0.65 mg/mL phenol, pH 7.4. The instrument aperture tube orifice size was 50 microns. Particle size data were collected for 50 seconds. The mean particle diameter of the crystals was approximately 6 microns, with an approximately normal distribution, encompassing a range of particle sizes from approximately 2 microns to approximately 12 microns. This result is similar to the particle size distribution of commercial NPH as reported in DeFelippis, M. R., et al., *J. Pharmaceut. Sci.* 87:170–176 (1998).

Preparation 20

Microcrystals of B29-Nε-nonanoyl-Human Insulin

Nε-nonanoyl-Human Insulin was prepared as described in Preparation 5. A sample of Nε-nonanoyl-human insulin (16.16 mg) was dissolved in 0.8 mL of 0.1 N HCl. The procedure described in Preparation 14 was followed, except the protamine solution contained 18.64 mg of protamine sulfate in a total volume of 50 mL. Rod-like crystals formed in high yield (greater than 80%). In the spectrophotometric dissolution assay described above, the crystals of B29-Nε-nonanoyl-human insulin had a t½ of 83 minutes, compared with about 6 minutes for Humulin® N in the same assay.

Preparation 21

Microcrystals of B29-Nε-decanoyl-Human Insulin

B29-Nε-decanoyl-human insulin was prepared essentially as described in Preparation 5. A sample of B29-Nε-decanoyl-human insulin (60.7 mg) was dissolved in 1.5 mL of 0.1 N HCl. A volume (0.6 mL) of a zinc nitrate solution containing 1000 parts-per-million (ppm) zinc(II) was added and mixed thoroughly. To 0.7 mL of the resulting solution in "Vial A" was added 2.0 mL of diluent "A" (50 mM citrate, 5 mg/mL phenol, 16 mg/mL glycerol, 25 mM TRIS, pH 7.6). To another 0.7 mL portion of the zinc-derivatized protein solution was added 2.0 mL of diluent "B" (100 mM citrate, 2 mg/mL phenol, 50 mM TRIS, pH 7.6). The pH in the vials was adjusted to 7.62 and 7.61, respectively, and each was filtered through a 0.22 micron, low-protein binding filter. A volume of the contents of vial A (2.5 mL) was mixed with 2.5 mL of a protamine sulfate solution (7.4 mg protamine sulfate dissolved in 10 mL of diluent A). A cloudy precipitate developed immediately. The preparation was allowed to stand undisturbed at 25° C. Likewise, a volume of the contents of vial B (2.5 mL) was mixed with 2.5 mL of a protamine sulfate solution (37.8 mg protamine sulfate dissolved in 50 mL of water). A cloudy precipitate developed immediately. The preparation was allowed to stand undisturbed at 25° C. Microscopic examination of the contents of both vials after 60 hours revealed that small crystals had formed in both. A rod-like morphology was clearly evident for the crystals in vial B. The yield of crystals in vial B was determined by HPLC to be 80%. In the spectrophotometric dissolution assay described above, the crystals of B29-Nε-decanoyl-human insulin in vial B had a t½ of 70 minutes, compared with about 6 minutes for Humulin® N in the same assay.

Preparation 22

Microcrystals of B29-Nε-dodecanoyl-Human Insulin

B29-Nε-dodecanoyl-human insulin was prepared as described in Preparation 5. A sample of B29-Nε-dodecanoyl-human insulin (17.00 mg) was dissolved in 4.0 mL of diluent (containing in an aqueous solution, per mL of solution, 10 mg phenol, 32 mg glycerol, 30 mg trisodium citrate dihydrate, and 6.1 mg TRIS, pH 8.47). The pH of the solution of the insulin analog derivative was adjusted to 8.57 using small aliquots of 1 N NaOH. To the pH-adjusted solution was added 0.320 mL of a zinc nitrate solution containing 1000 parts-per-million (ppm) zinc(II). The pH of the zinc-insulin analog derivative solution was adjusted to 7.59 using small aliquots of 1 N HCl and 1 N NaOH. The pH-adjusted solution was filtered through a 0.22 micron, low-protein binding filter. To 2.0 mL of the resulting solution in "Vial A" was added 0.25 mL of ethanol. The mixture was mixed gently. To another 2.0 mL volume of the resulting solution in "Vial B" was added 0.6 mL of ethanol. The mixture was mixed gently. To the contents of both Vial A and Vial B were added 2.0 mL of a protamine solution (containing, dissolved in water, 0.376 mg protamine per mL). After adding the protamine solution, each vial contained a cloudy suspension. Each vial was swirled gently to complete mixing, and then allowed to stand at 25° C. Small, irregular crystals formed in very high yield (greater than 90%). In the spectrophotometric dissolution assay described above, the crystals of B29-Nε-dodecanoyl-human insulin had a t½ of greater than 300 minutes, compared with about 6 minutes for Humulin® N in the same assay.

Preparation 23

Microcrystals of B29-Nε-tetradecanoyl-Human Insulin

B29-Nε-tetradecanoyl-human insulin was prepared as described in Preparation 5. A sample of B29-Nε-tetradecanoyl-human insulin (16.42 mg) was dissolved in 0.5 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of diluent (containing in an aqueous solution, per mL of solution, 10 mg phenol, 32 mg glycerol, 30 mg trisodium citrate dihydrate, and 6.1 mg TRIS, pH 7.58), and the resulting mixture was stirred until completely mixed. After mixing the zinc-insulin derivative solution with the diluent, the pH of the resulting solution was adjusted first to 7.9, and then back to 7.59, using small aliquots of 1 N HCl and 1 N NaOH, as needed. The pH-adjusted solution was filtered through a 0.22 micron, low-protein binding filter. To 1.97 mL of the resulting solution in "Vial A" was added 0.246 mL of ethanol. The mixture was mixed gently. To another 1.97 mL volume of the resulting solution in "Vial B" were added 0.591 mL of ethanol, which resulted in the formation of a haziness in the vial. The mixture was mixed gently. To the contents of both Vial A and Vial B were added 1.97 mL of a protamine solution (containing, dissolved in water, 0.376 mg protamine per mL). After adding the protamine solution, each vial contained a cloudy suspension. Each vial was swirled gently to complete mixing, and then allowed to stand at 25° C. Small, irregular crystals formed in very high yield (greater than 90%). In the spectrophotometric dissolution assay described above, the crystals of B29-Nε-tetradecanoyl-human insulin had a t½ of greater than 300 minutes, compared with about 6 minutes for Humulin® N in the same assay.

Preparation 24

Microcrystals of B29-Nε-hexadecanoyl-Human Insulin

B29-Nε-hexadecanoyl-human insulin was prepared as described in Preparation 5. A sample of B29-Nε- hexadecanoyl-human insulin (16.29 mg) was dissolved in 0.5 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of diluent (containing in an aqueous solution, per mL of solution, 10 mg phenol, 32 mg glycerol, 30 mg trisodium citrate dihydrate, and 6.1 mg TRIS, pH 7.58), and the resulting mixture was stirred until completely mixed. After mixing the zinc-insulin derivative solution with the diluent, the pH of the resulting solution was adjusted first to 8.0, and then back to 7.61, using small aliquots of 1 N HCl and 1 N NaOH, as needed. The pH-adjusted solution was filtered through a 0.22 micron, low-protein binding filter. To 2.0 mL of the resulting solution in "Vial A" was added 0.25 mL of ethanol. The mixture was mixed gently. To another 2.0 mL volume of the resulting solution in "Vial B" were added 0.6 mL of ethanol, which resulted in the formation of a haziness in the vial. The mixture was mixed gently. To the contents of both Vial A and Vial B were added 2.0 mL of a protamine solution (containing, dissolved in water, 0.376 mg protamine per mL). After adding the protamine solution, each vial contained a cloudy suspension. Each vial was swirled gently to complete mixing, and then allowed to stand at 25° C. Crystals formed in both vials. Small, irregular crystals formed in very high yield (greater than 90%). In the spectrophotometric dissolution assay described above, the crystals of B29-Nε-hexadecanoyl-human insulin had a t½ of greater than 300 minutes, compared with about 6 minutes for Humulin® N in the same assay.

Preparation 25

Microcrystals of A1-Nα-octanoyl-B29-Nε-octanoyl-Human Insulin

A mass (8.13 mg) of A1-Nα-octanoyl-B29-Nε-octanoyl-human insulin analog was dissolved in 1.60 mL of diluent (in 100 mL: 0.604 g TRIS, 1.003 g phenol, 3.218 g glycerol, and 3.069 g trisodium citrate). The pH of this solution was adjusted to 7.61 with small quantities of 1.0 N HCl and 1.0 N NaOH. After stirring for 5–10 minutes, 0.160 mL of a zinc nitrate solution containing 1000 parts-per-million (ppm) zinc(II) was added and the resulting solution was mixed again thoroughly. The pH was adjusted again, to 7.62, and then the solution was filtered through a 0.22 micron, low-protein binding filter. To 2 mL of this filtered solution was added 2 mL of a protamine solution (in 100 mL, 37.41 mg of protamine). The mixture was swirled gently. A precipitate formed. The mixture was left undisturbed at 25° C. Small irregular crystals formed.

Preparation 26

Microcrystals of A1-Nα-octanoyl-B29-Nε-octanoyl-desB30-Human Insulin

The process of Preparation 25 was followed essentially, except that 8.08 mg of A1-Nα-octanoyl-B29-Nε-octanoyl-desB30-human insulin was used. Small irregular crystals formed.

Preparation 27

Microcrystals of A1-Nα-nonanoyl-B29-Nε-nonanoyl-desB30-Human Insulin

The process of Preparation 25 was followed essentially, except that 8.07 mg of A1-Nα-nonanoyl-B29-Nε-nonanoyl-desB30-human insulin was used. Small irregular crystals formed.

Preparation 28

Microcrystals of A1-Nα-decanoyl-B29-Nε-decanoyl-desB30-Human Insulin

The process of Preparation 25 was followed essentially, except that 8.22 mg of A1-Nα-decanoyl-B29-Nε-decanoyl-desB30-human insulin was used. Small irregular crystals formed.

Preparation 29

Microcrystals of B29-Nε-octanoyl-Gly(A21),Arg(B31),Arg(B32)-Human Insulin Analog B29-Nε-octanoyl-Gly(A21),Arg(B31),Arg(B32)-human insulin analog was prepared as described in Preparation 5. A mass (8.6 mg) of B29-Nε-octanoyl-Gly(A21),Arg(B31),Arg(B32)-human insulin analog was dissolved in 0.4 mL of 0.1 N HCl. After stirring for 5–10 minutes, 0.160 mL of a zinc nitrate solution containing 1000 parts-per-million (ppm) zinc(II) was added and the resulting solution was mixed again thoroughly. Then, 1.60 mL of diluent (in 100 mL: 0.604 g TRIS, 1.003 g phenol, 3.218 g glycerol, and 3.069 g trisodium citrate) was added and mixed by additional stirring. The pH of this solution was adjusted to 7.59 with small quantities of 1.0 N HCl and 1.0 N NaOH, and then the solution was filtered through a 0.22 micron, low-protein binding filter. To 2 mL of this filtered solution was added 2 mL of a protamine solution (in 100 mL, 37.41 mg of protamine). The mixture was swirled gently. A precipitate formed. The mixture was left undisturbed at 25° C. Small irregular crystals formed.

Preparation 30

Microcrystals of B29-Nε-octanoyl-des(ThrB30)-Human Insulin

B29-Nε-octanoyl-des(ThrB30)-Human Insulin was prepared as described in Preparation 5. A sample of B29-Nε-octanoyl-des(ThrB30)-human insulin (16.21 mg) was dissolved in 0.5 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of diluent (containing in an aqueous solution, per mL of solution, 10 mg phenol, 32 mg glycerol, 30 mg trisodium citrate dihydrate, and 6.1 mg TRIS, pH 7.58), and the resulting mixture was stirred until completely mixed. After mixing the zinc-insulin derivative solution with the diluent, the pH of the resulting solution was adjusted first to 8.45 using small aliquots of 1 N NaOH, as needed. This failed to completely clarify the solution. The pH was then adjusted to 7.61, using small aliquots of 1 N HCl, as needed. The pH-adjusted solution was filtered through a 0.22 micron, low-protein binding filter. To a volume of the filtered solution was added an equal volume of an aqueous solution of protamine (containing, dissolved in water, 0.376 mg protamine per mL). After adding the protamine solution, a cloudy suspension developed. The suspension was swirled gently to complete mixing, and then allowed to stand at 25° C. Rod-like crystals formed in high yield (greater than 80%). In the spectrophotometric dissolution assay described above, the crystals of B29-Nε-octanoyl-des (ThrB30)-human insulin had a t½ of 94 minutes, compared with about 6 minutes for Humulin® N in the same assay.

Preparation 31

Microcrystals of B29-Nε-octanoyl-des(B30)-Human Insulin Analog

B29-Nε-octanoyl-des(ThrB30)-human insulin was prepared as described in Preparation 5. A sample of B29-Nε- octanoyl-des(ThrB30)-human insulin (8.09 mg) was dissolved in 0.400 mL of 0.1 N HCl. After stirring for 5–10 minutes, a volume (0.16 mL) of a zinc nitrate solution containing 1000 parts-per-million (ppm) zinc(II) was added, and the resulting solution was thoroughly mixed by stirring. After stirring for 5–10 minutes, 0.160 mL of a zinc nitrate solution containing 1000 parts-per-million (ppm) zinc(II) was added and the resulting solution was mixed thoroughly. Then, 1.60 mL of diluent (in 100 mL: 0.604 g TRIS, 1.003 g phenol, 3.218 g glycerol, and 3.069 g trisodium citrate) was added and mixed. The pH of this solution was adjusted to 7.61 with small quantities of 1.0 N HCl and 1.0 N NaOH, and then the solution was filtered through a 0.22 micron, low-protein binding filter. To 2 mL of this filtered solution was added 2 mL of a protamine solution (in 100 mL, 37.41 mg of protamine). The mixture was swirled gently. A precipitate formed. The mixture was left undisturbed at 25° C.

Preparation 32

Microcrystals of B29-Nε-hexanoyl-Beef Insulin

B29-Nε-hexanoyl-beef insulin was prepared as described in Preparation 5. A sample of B29-Nε-hexanoyl-beef insulin (16.14 mg) was dissolved in 0.8 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of crystallization diluent (containing, per mL, 10 mg phenol, 16 glycerol, 30 mg trisodium citrate dihydrate, and 6.0 mg TRIS, in water, pH unadjusted) was added, and the resulting mixture was stirred until completely mixed. After mixing the zinc-insulin derivative solution with the crystallization diluent, the pH of the resulting solution was adjusted to 7.58 using small aliquots of 1 N HCl and 1 N NaOH, as needed. The pH-adjusted solution was filtered through a 0.22 micron, low-protein binding filter. To a volume of the filtered solution was added an equal volume of an aqueous solution of protamine (0.375 mg protamine sulfate/mL solution, in water, pH not adjusted). The mixture of the two volumes was swirled gently to complete mixing. A cloudy suspension formed, which was gently swirled to complete mixing, and then allowed to stand at 25° C. Rod-like crystals formed in very high yield (greater than 90%). In the spectrophotometric dissolution assay described above, the crystals of B29-Nε-hexanoyl-beef insulin had a t½ of greater than 300 minutes, compared with about 6 minutes for Humulin® N in the same assay.

Preparation 33

Microcrystals of B29-Nε-hexanoyl-Sheep Insulin

B29-N -hexanoyl-sheep insulin was prepared as described in Preparation 5. A sample of B29-Nε-hexanoyl-sheep insulin (16.15 mg) was dissolved in 0.8 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. The solution was hazy, and the addition of 0.1 mL 0.1 N HCl did not cause the haze to disperse completely. The procedure of Preparation 32 was followed thereafter, except that the pH was adjusted to 7.61 instead of 7.58. Small, irregular crystals formed in high yield (greater than 80%). In the spectrophotometric dissolution assay described above, the crystals of B29-Nε-hexanoyl-sheep insulin had a t½ of 184 minutes, compared with about 6 minutes for Humulin® N in the same assay.

Preparation 34

Microcrystals of B29-Nε-octanoyl-Pork Insulin

B29-Nε-octanoyl-pork insulin was prepared as described in Preparation 5. A sample of B29-Nε-octanoyl-pork insulin (16.78 mg) was dissolved in 0.5 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of diluent (containing in an aqueous solution, per mL of solution, 10 mg phenol, 32 mg glycerol, 30 mg trisodium citrate dihydrate, and 6.1 mg TRIS, pH 8.5), and the resulting mixture was stirred until completely mixed. After mixing the zinc-insulin derivative solution with the diluent, the pH of the resulting solution was adjusted first to 8.4 using small aliquots of 1 N NaOH, as needed. The pH was then adjusted to 7.60, using small aliquots of 1 N HCl, as needed. After this, the procedure of Preparation 32 was followed. Small, irregular crystals formed in high yield (greater than 80%). In the spectrophotometric dissolution assay described above, the crystals of B29-Nε-octanoyl-pork insulin had a t½ of greater than 300 minutes, compared with about 6 minutes for Humulin® N in the same assay.

Preparation 35

Microcrystals of B29-Nε-octanoyl-Rabbit Insulin

B29-Nε-octanoyl-rabbit insulin was prepared as described in Preparation 5. A sample of B29-Nε-octanoyl-rabbit insulin (8.10 mg) was dissolved in 0.25 mL of 0.1 N HCl. After stirring for 5–10 minutes, a volume (0.16 mL) of a zinc nitrate solution containing 1000 parts-per-million (ppm) zinc(II) was added, and the resulting solution was thoroughly mixed by stirring. Then, 1.6 mL of diluent (containing in an aqueous solution, per mL of solution, 10 mg phenol, 32 mg glycerol, 30 mg trisodium citrate dihydrate, and 6.1 mg TRIS, pH 8.5), and the resulting mixture was stirred until completely mixed. After mixing the zinc-insulin derivative solution with the diluent, the pH of the resulting solution was adjusted first to 8.34 using small aliquots of 1 N NaOH, as needed. The pH was then adjusted to 7.57, using small aliquots of 1 N HCl, as needed. After this, the procedure of Preparation 32 was followed. Small, irregular crystals formed in high yield (greater than 80%). In the spectrophotometric dissolution assay described above, the crystals of B29-Nε-octanoyl-rabbit insulin had a t½ of 119 minutes, compared with about 6 minutes for Humulin® N in the same assay.

Preparation 36

Microcrystals of B29-Nε-octanoyl-des(B27)-Human Insulin Analog

B29-Nε-octanoyl-des(B27)-human insulin analog was prepared as described in Preparation 5. A mass (8.02 mg) of B29-Nε-octanoyl-des(B27)-human insulin analog was dissolved in 0.400 mL of 0.1 N HCl. After stirring for 5–10 minutes, 0.160 mL of a zinc nitrate solution containing 1000 parts-per-million (ppm) zinc(II) was added and the resulting solution was mixed thoroughly. Then, 1.60 mL of diluent (in 100 mL: 0.604 g TRIS, 1.003 g phenol, 3.218 g glycerol, and 3.069 g trisodium citrate) was added and mixed. The pH of this solution was adjusted to 7.61 with small quantities of 1.0 N HCl and 1.0 N NaOH, and then the solution was filtered through a 0.22 micron, low-protein binding filter. To 2 mL of this filtered solution was added 2 mL of a protamine solution (in 100 mL, 37.41 mg of protamine). The mixture was swirled gently. A precipitate formed. The mixture was left undisturbed at 25° C. After six days, well-formed, single, rod-shaped crystals formed.

Preparation 37

Microcrystals of B29-N$^\epsilon$-octanoyl-Asp(B28)-Human Insulin Analog

A mass (8.16 mg) of B29-N$\epsilon$-octanoyl-Asp(B28)-human insulin analog was dissolved in 1.60 mL of diluent (in 100 mL: 0.604 g TRIS, 1.003 g phenol, 3.218 g glycerol, and 3.069 g trisodium citrate). The pH of this solution was adjusted to 7.61 with small quantities of 1.0 N HCl and 1.0 N NaOH. After stirring for 5–10 minutes, 0.160 mL of a zinc nitrate solution containing 1000 parts-per-million (ppm) zinc(II) was added and the resulting solution was mixed again thoroughly. The pH was adjusted again, to 7.62, and then the solution was filtered through a 0.22 micron, low-protein binding filter. To 2 mL of this filtered solution was added 2 mL of a protamine solution (in 100 mL, 37.41 mg of protamine). The mixture was swirled gently. A precipitate formed. The mixture was left undisturbed at 25° C. Small, irregular crystals formed in high yield (greater than 80%). In the spectrophotometric dissolution assay described above, the crystals of B29-N$^\epsilon$-octanoyl-Asp(B28)-human insulin analog had a t½ of 15 minutes, compared with about 6 minutes for Humulin® N in the same assay.

Preparation 38

Microcrystals of B28-N$\epsilon$-butryl-LysB28,ProB29-Human Insulin

B28-N$\epsilon$-butryl-LysB28,ProB29-human insulin was prepared as described in Preparation 5. A sample of B28-N$\epsilon$-butryl-LysB28,ProB29-human insulin (16.09 mg) was dissolved in 0.8 mL of 0.1 N HCl. After stirring for 5–10 minutes, a volume (0.32 mL) of a zinc nitrate solution containing 1000 parts-per-million (ppm) zinc(II) was added, and the resulting solution was thoroughly mixed by stirring. Then, 3.2 mL of crystallization diluent was added, and the resulting mixture was stirred until completely mixed. (The crystallization diluent was prepared by dissolving in water, with stirring, 0.603 g of TRIS, 1.007 g of phenol, 1.582 g of glycerol and 2.947 g of trisodium citrate. Further water was added to bring the of the solution to 100 mL.) After mixing the zinc-insulin derivative solution with the crystallization diluent, the pH of the resulting solution was adjusted to 7.60 using small aliquots of 1 N HCl and 1 N NaOH, as needed. The pH-adjusted solution was filtered through a 0.22 micron, low-protein binding filter. To a volume of the filtered solution was added an equal volume of an aqueous solution of protamine, prepared by dissolving 18.64 mg of protamine sulfate in water to a final volume of 50 mL. The mixture of the two volumes was swirled gently to complete mixing, and then allowed to stand at 25° C.

Preparation 39

Microcrystals of B28-N$\epsilon$-hexanoyl-LysB28,ProB29-Human Insulin

B28-N$\epsilon$-hexanoyl-LysB28,ProB29-human insulin was prepared as described in Preparation 5. A sample of B28-N$\epsilon$-hexanoyl-LysB28,ProB29-human insulin (15.95 mg) was dissolved in 0.8 mL of 0.1 N HCl. The procedure of Preparation 38 was subsequently followed. Small, irregular crystals formed in high yield (greater than 80%). In the spectrophotometric dissolution assay described above, the crystals of B28-N$\epsilon$-hexanoyl-LysB28,ProB29-human insulin had a t½ of 5–6 minutes, compared with about 6 minutes for Humulin® N in the same assay.

Preparation 40

Microcrystals of B28-N$\epsilon$-hexanoyl-LysB28,ProB29-Human Insulin

B28-N$\epsilon$-hexanoyl-LysB28,ProB29-human insulin was prepared as described in Preparation 5. A sample of B28-N$\epsilon$-hexanoyl-LysB28,ProB29-human insulin (16.8 mg) was dissolved in 4.0 mL of diluent (containing in an aqueous solution, per mL of solution, 10 mg phenol, 32 mg glycerol, 30 mg trisodium citrate dihydrate, and 6.1 mg TRIS, pH 7.58). The pH of the solution of the insulin analog derivative was adjusted to 8.4 using small aliquots of 1 N NaOH. To the pH-adjusted solution was added 0.320 mL of a zinc nitrate solution containing 1000 parts-per-million (ppm) zinc(II). The pH of the zinc-insulin analog derivative solution was adjusted to 7.61 using small aliquots of 1 N HCl and 1 N NaOH. The pH-adjusted solution was filtered through a 0.22 micron, low-protein binding filter. To 2.0 mL of the resulting solution in "Vial A" was added 0.25 mL of ethanol. The mixture was mixed gently, and the solution became hazy. To another 2.0 mL volume of the resulting solution in "Vial B" was added 0.6 mL of ethanol. The mixture was mixed gently, and solution became hazy. To the contents of both Vial A and Vial B were added 2.0 mL of a protamine solution (containing, dissolved in water, 0.376 mg protamine per mL). After adding the protamine solution, each vial contained a cloudy suspension. Each vial was swirled gently to complete mixing, and then allowed to stand at 25° C. Crystals formed in both vials. The composition of the solution in Vial A was analyzed for the remaining concentration of insulin analog derivative, and the crystals were subjected to dissolution testing.

Preparation 41

Microcrystals of B28-N$\epsilon$-octanoyl-LysB28,ProB29-Human Insulin

B28-N$\epsilon$-octanoyl-LysB28,ProB29-human insulin was prepared as described in Preparation 5. A sample of B28-N$\epsilon$-octanoyl-LysB28,ProB29-human insulin (16.02 mg) was dissolved in 0.8 mL of 0.1 N HCl. Hereafter, the procedure of Preparation 38 was followed essentially. Small, irregular crystals formed in high yield (greater than 80%). In the spectrophotometric dissolution assay described above, the crystals of B28-N$\epsilon$-octanoyl-LysB28,ProB29-human insulin had a t½ of 7–8 minutes, compared with about 6 minutes for Humulin® N in the same assay.

Preparation 42

Microcrystals of B28-N$\epsilon$-octanoyl-LysB28,ProB29-Human Insulin

B28-N$\epsilon$-octanoyl-LysB28,ProB29-human insulin was prepared as described in Preparation 5. A sample of B28-N$\epsilon$-octanoyl-LysB28,ProB29-human insulin (16.35 mg) was dissolved in 4.0 mL of diluent (containing in an aqueous solution, per mL of solution, 10 mg phenol, 32 mg glycerol, 30 mg trisodium citrate dihydrate, and 6.1 mg TRIS, pH 7.58). The pH of the solution of the insulin analog derivative was adjusted to 8.4 using small aliquots of 1 N NaOH. To the pH-adjusted solution was added 0.320 mL of a zinc nitrate solution containing 1000 parts-per-million (ppm) zinc(II). The pH of the zinc-insulin analog derivative solution was adjusted to 7.62 using small aliquots of 1 N HCl and 1 N NaOH. The pH-adjusted solution was filtered through a 0.22 micron, low-protein binding filter. To 2.0 mL of the resulting solution in "Vial A" was added 0.25 mL of ethanol. The mixture was mixed gently, and the solution became hazy. To another 2.0 mL volume of the resulting solution in "Vial B" was added 0.6 mL of ethanol. The mixture was mixed gently, and solution became hazy. To the contents of both Vial A and Vial B were added 2.0 mL of a protamine solution (containing, dissolved in water, 0.376 mg protamine per mL). After adding the protamine solution, each vial contained a cloudy suspension. Each vial was swirled gently to complete mixing, and then allowed to stand at 25° C. Crystals formed in both vials. The composition of the solution in Vial A was analyzed for the remaining concentration of insulin analog derivative, and the crystals were subjected to dissolution testing. Small, irregular crystals formed in high yield (greater than 80%). In the spectrophotometric dissolution assay described above, the crystals of B29-Nε-octanoyl-rabbit insulin had a t½ of 15 minutes, compared with about 6 minutes for Humulin® N in the same assay.

Preparation 43

Amorphous Suspension of B29-Nε-octanoyl-Human Insulin

B29-Nε-octanoyl-human insulin was prepared as described in Preparation 5. A sample of B29-Nε-octanoyl-human insulin (20.31 mg of solid, containing 16.95 mg protein) was dissolved in 0.5 mL of 0.1 N HCl. Then 200 microliters of a zinc nitrate solution containing 1000 parts-per-million (ppm) zinc(II) was added, followed by 2.0 mL of a diluent containing per mL: 1.625 mg phenol, 4 mg m-cresol, 40 mg glycerol, 5 mg anhydrous sodium dibasic phosphate, and 7.5 mg trisodium citrate dihydrate, with a final pH of 7.6. After adding the diluent, the pH of the resulting solution was adjusted to 7.58 with 0.090 mL of 1 N NaOH. The solution was then passed through a 0.22 micron, low-protein-binding sterile filter, and refrigerated overnight. At this point, the concentration of the insulin derivative was 6.074 mg/mL. The next morning, the solution had no visible precipitate. A volume of the solution (2.50 mL) was mixed with 2.875 mL of a protamine sulfate solution containing per mL 0.75 mg of solid protamine sulfate in water, and an amorphous precipitate immediately formed. The concentration of B29-Nε-octanoyl-human insulin was 2.825 mg/mL after adding protamine. The suspension was injected into two dogs approximately 1 hour and forty minutes after mixing the insulin derivative with protamine.

Preparation 44

Amorphous Suspension of B28-Nε-myristoyl-LysB28,ProB29 Human Insulin Analog

B28-Nε-myristoyl-LysB28,ProB29-human insulin was prepared essentially as described in Preparation 5. A sample of B28-Nε-myristoyl-LysB28,ProB29-human insulin (20.43 mg of solid, 18.53 mg of protein) was dissolved in 0.5 mL of 0.1 N HCl. Then 200 microliters of a zinc nitrate solution containing 1000 parts-per-million (ppm) zinc(II) and 2.0 mL of formulation diluent were added. The formulation diluent contained, per mL: 1.6 mg phenol, 4 mg m-cresol, 40 mg glycerol, 5 mg anhydrous sodium dibasic phosphate, and 7.5 mg trisodium phosphate dihydrate, with a final pH of 7.6. The pH of the formulation was adjusted from 5.9 to 8.7 with 100 microliters of 1 N NaOH. The formulation was clear. The pH was then reduced to 7.59 by adding 20 microliters of 1 N HCl. At this point, the protein concentration was 6.57 mg/mL. The solution was filtered through a 0.22 micron, low-protein binding sterile filter and refrigerated overnight. The next morning, the formulation had no visible precipitate present. A portion of the solution (2.50 mL) was mixed with 2.875 mL of protamine solution (0.75 mg/mL of solid protamine sulfate dissolved in water) and an amorphous suspension formed. The concentration of B28-Nε-myristoyl-LysB28,ProB29-human insulin would have been reduced to 3.056 mg/mL by the addition of the protamine solution. Samples for HPLC analysis were prepared promptly after the protamine was added. Based on known peak retention times, the HPLC analysis showed that the insoluble material contained protamine and B28-Nε-myristoyl-LysB28,ProB29-human insulin. The concentration of B28-Nε-myristoyl-LysB28,ProB29-human insulin in the supernatant was found to be 0.005 mg/mL, and in a sample of the precipitate re-dissolved to the original volume, the concentration was 3.13 mg/mL. The concentration of B28-Nε-myristoyl-LysB28,ProB29-human insulin in a sample of acidified suspension was 3.34 mg/mL.

Preparation 45

Microcrystals of B29-Nε-octanoyl-Human Insulin

A dry powder of B29-Nε-octanoyl-human insulin (7 parts by mass) is dissolved in 175 parts by volume of 0.1 N HCl, and then a solution of zinc chloride (60 parts by volume, prepared by dissolving zinc oxide in HCl to give a 15.3 mM concentration of zinc) is added. To this solution is added 800 parts by volume of an aqueous solvent comprising 25 mM TRIS, 10 mg/mL phenol, 0.1 M citrate, 40 mg/mL glycerol, in water at pH value 7.6. The resulting solution is adjusted to pH value of 7.6, and then filtered through a 0.22 micron, low-protein binding filter.

An additional solution is prepared by dissolving 7 parts by mass of protamine sulfate in 10,000 parts by volume of water. The protamine solution is filtered through a 0.22 micron, low-protein binding filter. Equal volumes of the derivatized protein solution and the protamine solution are combined by adding the protamine solution to the acylated insulin solution. An amorphous precipitate forms. This suspension is allowed to stand undisturbed for 48 hours at a temperature of 25° C. The microcrystals in the resulting preparation will provide extended and flatter time action compared with an equal dose of NPH human insulin.

Preparation 46

Microcrystals of B29-Nε-octanoyl-Human Insulin

The process of Preparation 45 is followed. The suspension is allowed to stand undisturbed for 48 hours at a temperature of 30° C. Similar results are obtained.

Preparation 47

Microcrystals of B29-Nε-octanoyl-Human Insulin

A dry powder of B29-Nε-octanoyl-human insulin (7 parts by mass) is dissolved in 175 parts by volume of 0.1 N HCl, and then a solution of zinc chloride (60 parts by volume, prepared by dissolving zinc oxide in HCl to give a 15.3 mM concentration of zinc) is added. To this solution is added 1000 parts by mass of an aqueous solvent comprising 35 mM sodium phosphate dibasic, 4 mg/mL m-cresol, 1.6 mg/mL phenol, 25 mM citrate, and 40 mg/mL glycerol, in water, pH 7.6. The resulting solution is adjusted to pH 7.6, and then filtered through a 0.22 micron, low-protein binding filter.

An additional solution is prepared by dissolving 6 parts by mass of protamine sulfate in 10,000 parts by volume of water then filtering through a 0.22 micron, low-protein binding filter. Equal volumes of the derivatized insulin solution and the protamine solution are combined by adding the protamine solution to the acylated protein solution. An amorphous precipitate forms. This suspension is allowed to stand undisturbed for 1 week at a temperature of 25° C. The microcrystals in the resulting preparation will provide extended and flatter time action compared with an equal dose of NPH human insulin.

Preparation 48

Microcrystals of B29-Nε-octanoyl-Human Insulin

A dry powder of B29-Nε-octanoyl-human insulin (7 parts by mass) is dissolved in 175 parts by volume of 0.1 N HCl, and then a solution of zinc chloride (60 parts by volume, prepared by dissolving zinc oxide in HCl to give a 15.3 mM concentration of zinc) is added. To this solution is added 1000 parts by mass of a solvent comprising 35 mM sodium phosphate dibasic, 4 mg/mL m-cresol, 1.6 mg/mL phenol, 10 mM citrate, 40 mg/mL glycerol, in water, pH 7.6. The resulting solution is adjusted to pH 7.6, and then filtered through a 0.22 micron, low-protein binding filter.

An additional solution is prepared by dissolving 6 parts by mass of protamine sulfate in 10,000 parts by volume of water then filtering through a 0.22 micron, low-protein binding filter. Equal volumes of the acylated insulin solution and the protamine solution are combined by adding the protamine solution to the acylated insulin solution. An amorphous precipitate forms. This suspension is allowed to stand undisturbed for 1 week at a temperature of 25° C. The microcrystals in the resulting preparation will provide extended and flatter time action compared with an equal dose of NPH human insulin.

Preparation 49

Microcrystals of B29-Nε-octanoyl-Human Insulin

The process of Preparation 47 is followed. The suspension is allowed to stand undisturbed for 60 hours at a temperature of 30° C. The microcrystals in the resulting preparation will provide extended and flatter time action compared with an equal dose of NPH human insulin.

Preparation 50

Microcrystals of B29-Nε-octanoyl-Human Insulin

A solution is prepared by adding to water for injection (WFI, 1000 parts by volume): phenol (0.65 parts by mass), m-cresol (1.6 parts by mass) and glycerin (16 parts by mass). Protamine sulfate powder (0.6 parts by mass) is then dissolved in this solution. A solution of zinc chloride (60 parts by volume) prepared by dissolving zinc oxide in HCl to give a 15.3 mM concentration of zinc in 0.1 N HCl is then added. A dry powder of B29-Nε-octanoyl-human insulin (7 parts by mass) is added and dissolved with stirring. The pH is adjusted to about 3 to aid dissolution if necessary with small quantities of 1 N HCl and 1 N NaOH. The pH is then adjusted to within the range 3–3.6 with small quantities of 1 N HCl and 1 N NaOH. This solution is filtered through a 0.22 micron, low-protein binding filter.

A second solution is prepared by dissolving sodium phosphate dibasic (7.56 parts by mass), phenol (0.65 parts by mass), m-cresol (1.6 parts by mass) and glycerin (16 parts by mass) in water for injection (1000 parts by volume). The pH of this solution is adjusted to a value such that combination of a volume of this solution with an equal volume of the B29-Nε-octanoyl-human insulin solution results in a pH value of about 7.5 to about 7.7. After appropriately adjusting the pH of this buffer solution, it is filtered through a 0.22 micron, low-protein binding filter. Equal volumes of the buffer solution and the B29-Nε-octanoyl-human insulin solution are combined. An amorphous precipitate forms immediately which becomes crystalline upon standing for 60 hours undisturbed at a controlled temperature of 25° C. The microcrystals in the resulting preparation will provide extended and flatter time action compared with an equal dose of NPH human insulin.

Preparation 51

Microcrystals of B29-Nε-octanoyl-Human Insulin

A solution is prepared by adding to water for injection (1000 parts by volume) sodium phosphate dibasic (3.78 parts by mass), phenol (0.65 parts by mass), m-cresol (1.6 parts by mass) and glycerin (16 parts by mass). A solution of zinc chloride (6 parts by volume) prepared by dissolving zinc oxide in HCl to give a 153 mM concentration of zinc in 0.1 N HCl is then added. A dry powder of B29-Nε-octanoyl-human insulin (7 parts by mass) is added and dissolved with stirring. The pH is adjusted to about 3 to aid dissolution if necessary with small quantities of 1 N HCl and 1 N NaOH. The pH is then adjusted to 7.6 with 10% HCl and 10% NaOH. This solution is filtered through a 0.22 micron, low-protein binding filter.

A second solution is prepared by dissolving sodium phosphate dibasic (3.78 parts by mass), phenol (0.65 parts by mass), m-cresol (1.6 parts by mass) and glycerin (16 parts by mass) in water for injection (1000 parts by volume). Protamine sulfate powder (0.6 parts by mass) is then dissolved in this solution. The pH of this solution is adjusted to 7.6. This solution is filtered through a 0.22 micron, low-protein binding filter. Equal volumes of this protamine solution and the B29-Nε-octanoyl-human insulin solution are combined. An amorphous precipitate forms immediately which becomes crystalline upon standing for 60 hours undisturbed at a controlled temperature of 25° C. The microcrystals in the resulting preparation will provide extended and flatter time action compared with an equal dose of NPH human insulin.

Preparation 52

Microcrystals of B29-Nε-(2-ethylhexanoyl)-Human Insulin

B29-Nε-(2-ethylhexanoyl)-human insulin was prepared as described in Preparation 5. A mass (8.00 mg) of B29-Nε-(2-ethylhexanoyl)-human insulin was dissolved in 0.400 mL of 0.1 N HCl. Thereafter, the procedure of Preparation 17 was followed essentially. A precipitate formed. The mixture was left undisturbed at 25° C. Rod-like crystals formed in high yield (greater than 80%). In the spectrophotometric dissolution assay described above, the crystals of B29-Nε-2-ethylhexanoyl-human insulin had a t½ of 34–35 minutes, compared with about 6 minutes for Humulin® N in the same assay.

EXAMPLE 1

In Vivo Testing in Diabetic Dogs

The protracted action of a suspension formulation containing microcrystals prepared as described in any of Preparations herein is tested in diabetic dogs by comparing its ability to control hyperglycemia with that of control compounds. A one-per-day dose of about 0.2 units/kg of body weight is used. This dose would be equivalent to about 1.2 nmol/kg. On test days, blood glucose is monitored for 24 hours following subcutaneous injection of the suspension formulation. Control compounds are human insulin and NPH human insulin. Suspension formulations of microcrystals of the present invention will reduce blood glucose levels and will have an extended time action compared with human insulin NPH when tested at comparable doses.

EXAMPLE 2

Time-Action of Crystals in Rats

To 1.898 mL of the crystal formulation prepared according to Preparation 19 was added 3.102 mL of a diluent (16 mg/mL glycerol, 20 mM TRIS, 1.6 mg/mL m-cresol, 0.65 mg/mL phenol, 40 mM trisodium citrate, pH 7.4). This provided 5 mL of a U40 formulation, which was tested in BBDP/Wor rats, a genetically-characterized animal model, maintained by, and available from, the University of Massachusetts Medical Center (Worchester, Mass.) in connection with Biomedical Research Models, Inc. (Rutland, Mass.). The DPBB/Wor rat line is diabetes-prone, and exhibits insulin-dependent (autoimmune) diabetes mellitus.

Forty BBDP/Wor rats [20 male/20 female, aged 4–5 months, maintained on a long-acting insulin (PZI)], were randomly assigned by gender to eight experimental groups, A, B, C, D, E, F, G, and H. Groups A (5 males) and B (5 females) were treated for two days with a U40 human insulin ultralente composition having 2.5 mg/mL zinc. Groups C (5 males) and D (5 females) were treated for two days with a U40 human insulin ultralente composition having 1.25 mg/mL zinc. Groups E (5 males) and F (5 females) were treated for two days with a U40 beef-pork PZI insulin (PZI). Groups G (5 males) and H (5 females) were treated for two days with a crystal formulation according to the present invention, as described in this example. Each rat was given daily injections of its group's formulation for the two days before blood glucose was determined, and on the day that the blood glucose was determined.

Blood was obtained half an hour before administering the test formulations. Animals were injected subcutaneously with either 0.9 U/100 g body weight (males) or 1.1 U/100 g body weight (females) at 11:30 A.M. Blood was obtained by nicking the tail (not anaesthetized), stored briefly on ice, centrifuged, and glucose determined using a Beckman II glucose analyzer. Blood samples were obtained just prior to administering the test formulations, and at 2, 4, 6, 8, 12, 16, 20, and 24 hours after administration. The crystal formulations of the present invention controlled blood glucose for a time comparable to that obtained with the long-acting insulin preparations.

EXAMPLE 3

Time-Action of Crystals in Rats

The testing procedure described above in Example 2 was repeated with a second 5 mL sample of a U40 formulation of a suspension, prepared as described above.

Thirty-five BBDP/Wor rats [18 male/17 female, age 4–5 months, maintained on a long-acting insulin (PZI)], were randomly assigned by gender to six experimental groups, I, J, K, L, M, and N. Groups I (8 males) and J (8 females) were treated for three days with the crystal formulation according to the present invention, as described in this example, above. Groups K (5 males) and L (4 females) were treated for three days with a U40 human insulin ultralente composition having 2.5 mg/mL zinc. Groups M (5 males) and N (5 females) were treated for three days with a U40 beef-pork PZI insulin (PZI). Each rat was given daily injections of its group's formulation for the three days before blood glucose was determined, and on the day that the blood glucose was determined.

Blood was obtained half an hour before administering the test formulations. Animals were injected subcutaneously with either 0.9 U/100 g body weight (males) or 1.1 U/100 g body weight (females) at 11:30 A.M. Blood was obtained by nicking the tail (not anaesthetized), stored briefly on ice, centrifuged, and glucose determined using a Beckman II glucose analyzer. Blood samples were obtained just prior to administering the test formulations, and at 2, 4, 6, 8, 12, 16, 20, and 24 hours after administration. The crystal formulations of the present invention controlled blood glucose for a time comparable to that obtained with the long-acting insulin preparations.

EXAMPLE 4

Time-Action of Crystals in Rats

Twenty-six BBDP/Wor rats [13 male/13 female, age 4–6 months, maintained on a long-acting, protamine zinc insulin (PZI)], were randomly assigned by gender to four experimental groups, O, P, Q, and R. Groups O (8 males) and P (8 females) were treated for three days with the crystal formulation according to the present invention, as described in Example 2. Groups Q (5 males) and R (5 females) were treated for three days with a U-40 beef-pork PZI insulin (PZI). Each rat was given daily injections of its group's formulation for the three days before blood glucose was determined, and on the day that the blood glucose was determined.

Blood was obtained half an hour before administering the test formulations. Animals were injected subcutaneously with either 0.9 U/100 g body weight (males) or 1.1 U/100 g body weight (females) at 11:30. Blood was obtained by nicking the tail (not anaesthetized), stored briefly on ice, centrifuged, and glucose determined using a Beckman II glucose analyzer. Blood samples were obtained just prior to administering the test formulations, and at 2, 4, 6, 8, 12, 16, 20, and 24 hours after administration. The crystal formulations of the present invention controlled blood glucose for a time comparable to that obtained with the long-acting insulin preparations.

EXAMPLE 5

Amorphous Precipitate of B29-Nε-octanoyl-Human Insulin Tested in Dogs

The time action of a formulation containing an amorphous precipitate of protamine and B29-Nε-octanoyl-human insulin, prepared as described in Preparation 43, was determined in two normal dogs (2 nmol/kg, subcutaneous). The dogs received a constant infusion of somatostatin to create a transient diabetic state. The data were compared with those observed in the same model after administration of human insulin ultralente (3 nmol/kg, n=5), and with saline (n=6).

Experiments were conducted in overnight-fasted, chronically-cannulated, conscious male and female beagles weighing 10–17 kg (Marshall Farms, North Rose, N.Y.). At least ten days prior to the study, animals were anesthetized with isoflurane (Anaquest, Madison, Wis.), and silicone catheters attached to vascular access ports (V-A-P™, Access Technologies, Norfolk Medical, Skokie, Ill.) were inserted into the femoral artery and femoral vein. The catheters were filled with a glycerol/heparin solution (3:1, v/v; final heparin concentration of 250 kIU/mL; glycerol from Sigma Chemical Co., St. Louis, Mo., and heparin from Elkins-Sinn, Inc., Cherry Hill, N.J.) to prevent catheter occlusion, and the wounds were closed. Kefzol (Eli Lilly & Co., Indianapolis, Ind.) was administered pre-operatively (20 mg/kg, IV and 20 mg/kg, I.M.), and Keflex was administered post-operatively (250 mg, p.o. once daily for seven days) to prevent infections. Torbugesic (1.5 mg/kg, I.M.) was administered post-operatively to control pain.

Blood was drawn just prior to the study day to determine the health of the animal. Only animals with hematocrits above 38% and leukocyte counts below 16,000/mm$^3$ were used (hematology analyzer: Cell-Dyn 900, Sequoia-Turner, Mountain View, Calif.).

The morning of the experiment, the ports were accessed (Access Technologies, Norfolk Medical, Skokie, Ill.); the contents of the catheters were aspirated; the catheters were flushed with saline (Baxter Healthcare Corp., Deerfield, Ill.); the dog was placed in a cage; and extension lines (protected by a stainless steel tether and attached to a swivel system [Instech Laboratories, Plymouth Meeting, Pa.]) were attached to the port access lines.

Dogs were allowed at least 10 minutes to acclimate to the cage environment before an arterial blood sample was drawn for determination of fasting insulin and blood glucose concentrations (time=−30 minutes). At this time, a continuous, IV infusion of cyclic somatostatin (0.65 μg/kg/min; BACHEM California, Torrance, Calif.) was initiated and continued for the next 30.5 hours. Thirty minutes after the start of infusion (time=0 minutes), an arterial blood sample was drawn, and a subcutaneous bolus of test substance, or vehicle, was injected in the dorsal aspect of the neck. Arterial blood samples were taken every 3 hours thereafter for the determination of plasma glucose and insulin concentrations.

Arterial blood samples were collected in vacuum blood collection tubes containing disodium EDTA (Terumo Medical Corp., Elkton, Md.) and immediately placed on ice. The samples were centrifuged, and the resulting plasma was transferred to polypropylene test tubes and stored on ice for the duration of the study.

Plasma glucose concentrations were determined the day of the study using a glucose oxidase method in a Beckman glucose analyzer (Beckman Instruments, Inc., Brea, Calif.). Samples for other assays were stored at −80° C. until time for analysis. Insulin concentrations were determined using a double antibody radioimmunoassay.

At the conclusion of the experiment, the catheters were flushed with fresh saline, treated with Kefzol (20 mg/kg), and filled with the glycerol/heparin mixture; antibiotic (Keflex; 250 mg) was administered p.o. To minimize the number of animals being used and to allow pairing of the data base when possible, animals were studied multiple times. Experiments in animals being restudied were carried out a minimum of one week apart.

The formulation of amorphous precipitate of B29-Nε-octanoyl-human insulin, prepared as described above, provided effective control of blood glucose for almost 27 hours, compared with only about 21 hours for human insulin ultralente. The precipitate provided a significantly flatter and a more extended control of glucose levels than did human insulin ultralente. For example, the nadir of the blood glucose concentration was obtained after 1.5 hours for the precipitate, and then the glucose level rose to a fairly constant level. By comparison, the nadir for human insulin ultralente was reached after 9 hours, and after that, the blood glucose level rose relatively quickly. The glucose level at the nadir was 72 mg/dL for the derivatized insulin precipitate formulation, while it was 56 mg/dL for the ultralente formulation. Finally, plasma insulin levels corroborate these observations, and correlate well with the greater flatness and extension of time action of the amorphous precipitate of B29-Nε-octanoyl-human insulin compared with human insulin ultralente.

EXAMPLE 6

Microcrystals of B29-Nε-octanoyl-Human Insulin Tested in Dogs

The glucodynamics of two formulations containing crystals of B29-Nε-octanoyl-human insulin, prepared as described in Preparation 19, or essentially as described in Preparation 19 was determined in in normal dogs, using essentially the protocol described in Example 5. One of two preparations of microcrystals was administered to each dog at a dose of 2 nmol/kg subcutaneously. The experiments were carried out one three different occasions. The data from these three experiments were combined. A total of ten dogs each received a 2 nmol/kg dose of one of two preparations. In a separate experiment, a dose of a formulation of microcrystals of B29-Nε-octanoyl-human insulin prepared essentially as described in Preparation 19 was administered subcutaneously to each of five dogs at a dose of 3 nmol/kg. Human insulin NPH (2 nmol/kg, n=5), and saline vehicle (n=5) served as controls. In each experiment, the dogs received a constant infusion of somatostatin to create a transient diabetic state.

The formulation of microcrystals comprising B29-Nε-octanoyl-human insulin, administered at 2 nmol/kg, had an effective time action of 27 hours, compared with 21 hours for human insulin NPH at the same dose. The glucodynamic profile showed less hypoglycemic tendency than human insulin NPH, which is an advantageous quality. At 3 nmol/kg, the microcrystals comprising B29-Nε-octanoyl-human insulin effectively controlled glucose levels for at least 30 hours. At the glucose nadir, about the same glucose level was obtained as that obtained after administration of human insulin NPH (namely, about 65 mg/dL). However, the duration of such depressed glucose levels was much shorter for the microcrystals comprising B29-Nε-octanoyl-human insulin (about 3 hours) compared with human insulin NPH (about 7.5 hours). After the nadir, blood glucose levels for the group receiving microcrystals comprising B29-Nε-octanoyl-human insulin varied only between 91 and 115 mg/dL up to 30 hours, after which no further data are available. In contrast, glucose levels in the group the received human insulin NPH at 2 nmol/kg varied from 89 to 145 after the nadir was reached.

EXAMPLE 7

Microcrystals of B29-Nε-hexanoyl-Human Insulin Tested in Dogs

The glucodynamics of formulations containing crystals of B29-Nε-hexanoyl-human insulin, prepared as described in Preparation 16, was determined in normal dogs, using essentially the protocol described in Example 5. The formulation of microcrystals comprising B29-Nε-hexanoyl-human insulin, administered at 2 nmol/kg had an effective time action of 24 hours, compared with 24 hours for human insulin NPH at the same dose. The glucodynamic profile was flatter, showing less hypoglycemic tendency than human insulin NPH. At the glucose nadir, about the same glucose level was obtained as that obtained after administration of human insulin NPH (namely, about 67 mg/dL, versus 64 mg/dL for human insulin NPH). However, the duration of such depressed glucose levels was much shorter for the microcrystals comprising B29-Nε-hexanoyl-human insulin (about 3 hours) compared with human insulin NPH (about 7.5 hours).

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

I claim:

1. A pharmacologically-active microcrystal comprising (a) a deriviated protein selected from the group consisting of deriviated insulin, deriviated insulin analogs, and deriviated proinsulins; (b) a complexing compound; (c) a hexamer-stabilizing compound; and (d) a divalent metal cation.

2. The microcrystal of claim 1, wherin the complexing compound is protamine.

3. The microcrystal of claim 1 wherein the divalent metal cation is zinc.

4. The microcrystal of claim 1 wherein the derivatized protein is an insulin acylated at the BLys29-N-ε position with a fatty acid.

5. The microcrystal of claim 4, wherein the fatty acid is a straight-chain saturated fatty acid.

6. The microcrystal of claim 5 wherein the fatty acid is selected from the group consisting of n-hexanoic acid, n-heptanoic acid, n-octanoic acid, n-nonanoic acid, and n-decanoic acid.

7. The microcrystal of claim 6 wherein the deriviated insulin is selected from the group consisting of B29-Nε-hexanoyl-human insulin, B29-Nε-octanoyl-human insulin, and B29-Nε-octanoyl-human insulin, and B29-Nε-decanoyl-human insulin.

8. The microcrystal of claim 4, wherein the deriviated protein is acylated with a fatty acid selected from the group consisting of n-dodecanoic acid, n-tetradecanoic acid, and n-hexadecanoic acid.

9. The microcrystal of claim 5, further comprising a second acylation at an Nα-amino group in addition to the LysB29-N-∞ position, wherein the di-acylation occurs with a fatty acid selected from the group consisting of n-hexanoic acid, n-heptanoic acid, n-octanoic acid, n-nonanoic acid, and n-decanoic acid.

10. The microcrystal of claim 4, wherein the deriviated protein is insulin that is acylated with a branched-chain, saturated fatty acid.

11. The microcrystal of claim 10, wherein the branched saturated fatty acid has from three to ten carbon atoms in its largest branch.

12. The microcrystal of claim 1, wherein the deriviated protein is selected from the group consisting of fatty acid-acylated animal insulins, fatty acid-acylated monomeric insulin analogs, fatty acid-acylated deletion analogs, and fatty acid-acylated pI-shifted insulin analogs.

13. The microcrystal of claim 12, wherein the derivatized protein is fatty acid-acylated des(B30)-human insulin analog, fatty acid-acylated LysB28,ProB29-human insulin analog, or fatty acid-acylated AspB28-human insulin analog.

14. The microcrystal of claim 13, wherein the derivatized protein is fatty acid-acylated des B(30)-human insulin analog.

15. The microcrystal of claim 12, wherein the derivatized protein is acylated with a fatty acid selected from the group consisting of n-dodecanoic acid, n-tetradecanoic acid, and n-hexadecanoic acid.

16. The microcrystal of claim 15, wherein the derivitized protein is fatty acod-acylated des (B30)-human insulin analog, fatty acid-acylated AspB28-human insulin analog.

17. The microcrystal of claim 16, wherein the derivatized protein is fatty acid-acylated des (B30)-human insulin analog.

18. The microcrystal of claim 17, wherein the derivatized protein is B29-N∞-myristoyl-des (B30)-human insulin analog.

19. The microcrystal of claim 16, wherein the derivatized protein is B28-N∞-myristoyl-LysB28, ProB29-human insulin analog.

20. The microcrystal of claim 12, wherein the derivatized protein is an insulin analog that is acylated with a branched-chain, saturated fatty acid.

21. The microcrystal of claim 20, wherein the branched chain, saturated fatty acid has from three to ten carbon atoms in its longest branch.

22. The microcrystal of claim 1, wherein the microcrystal has rod-like morphology.

23. The microcrystal of claim 1, wherein the microcrystal has irregular morphology.

24. The microcrystal of claim 1, wherein the hexamer stabilizing solution is a phenolic composition.

* * * * *

UNITED STATES PATENT AND TRADEMARK OFFICE
CERTIFICATE OF CORRECTION

PATENT NO.   : 6,268,335 B1                                                Page 1 of 1
DATED        : July 31, 2001
INVENTOR(S)  : Mark Laurence Brader It is certified that error appears in the above-identified patent and that said Letters Patent is hereby corrected as shown below:

Column 55,
Line 26, "(a) a deriviated protein" should read -- (a) a derivatized protein --.
Line 27, "deriviated insulin, deriviated insulin analogs, and deriviated" should read
-- derivatized insulin, derivatized insulin analogs, and derivatized --.
Line 35, "at the BLys29-N-∈" should read -- at the LysB29-N-∈ --.
Line 43, "wherein the deriviated" should read -- wherein the derivatized --.
Line 46, "and B29-N∈-octanoyl-human insulin, and B29-N∈-" should read
-- and B29-N∈- --.
Line 48, "wherein the deriviated" should read -- wherein the derivatized --.
Line 53, "acylation at an N√-amino group" should read -- acylation at an Nα-amino group --.

Column 56,
Line 1, "LysB29-N-∞ position," should read -- LysB29-N∈ position, --.
Line 5, "wherein the deriviated" should read -- wherein the derivatized --.
Line 11, "wherein the deriviated" should read -- wherein the derivatized --.
Line 29, "acod-acylated" should read -- acid-acylated --.
Line 30, "analog, fatty acid-acylated AspB28-human insulin analog." should read
-- analog, fatty acid-acylated LysB28, ProB29-human insulin analog, or fatty acid-acylated AspB28-human insulin analog. --.

Signed and Sealed this

Thirteenth Day of August, 2002

Attest:

Attesting Officer

JAMES E. ROGAN
Director of the United States Patent and Trademark Office